(12) United States Patent
Shyur et al.

(10) Patent No.: US 9,493,751 B2
(45) Date of Patent: Nov. 15, 2016

(54) DUAL-FUNCTIONAL HYBRID GLUCANASES

(71) Applicant: Academia Sinica, Taipei (TW)

(72) Inventors: Lie-Fen Shyur, Taipei (TW);
Wei-Chun Liu, Kaohsiung (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/212,231

(22) Filed: Mar. 14, 2014

(65) Prior Publication Data
US 2014/0273154 A1 Sep. 18, 2014

Related U.S. Application Data

(60) Provisional application No. 61/789,804, filed on Mar. 15, 2013.

(51) Int. Cl.
*C12N 9/24* (2006.01)
(52) U.S. Cl.
CPC ................... *C12N 9/2405* (2013.01)
(58) Field of Classification Search
None
See application file for complete search history.

(56) References Cited

U.S. PATENT DOCUMENTS

| 7,527,958 B2 | 5/2009 | Shyur et al. | |
| 2009/0220480 A1* | 9/2009 | Gray et al. | 424/94.61 |

OTHER PUBLICATIONS

Lin et al. FASEB J. (2006) 20 (5), Part 2, pp. A898.*
Borriss, et al., "Hybrid Bacillys Endo-(1-3,1-4)-β-Glucanases: Construction of Recombinant Genes and Molecular Properties of the Gene Products", Carlsberg Res. Commun., vol. 54, pp. 41-54, 1989.
Chen, et al., "Domain-swapping of mesophilic xylanase with hyperthermophilic glucanase", BMC Biotechnology, vol. 12, p. 28, 2012.
Furtado, et al., "A designed bifunctional laccase/β-1,3-1,4-glucanase enzyme shows synergistic sugar release from milled sugarcane bagasse", Protein Engineering, Design & Selection, vol. 26, No. 1, pp. 15-23, 2013.
Jeng, et al., "Crystal Structures of the Laminarinase Catalytic Domain from *Thermotogo maritime* MSB8 in Complex with Inhibitors", Journal of Biological Chemistry vol. 286, No. 52, pp. 45030-45040, 2011.
Liu, et al., "Engineering of dual-functional hybrid glucanases", Protein Engineering, Design & Selection, pp. 1-10, 2012.
Meldgaard, et al., "Different effects of N-glycosylation on the thermostability of highly homologous bacterial (1-3,1-4)-β-glucanases secreted from yeast", Microbiology, vol. 140, pp. 159-166, 1994.
Musiychuk, et al., "Preparation and Properties of *Clostridium thermocellum* Lichenase Deletion Variants and Their Use for Construction of Bifunctional Hybrid Proteins", Biochemistry (Moscow), vol. 65, No. 12, pp. 1397-1402, 2000.
Politz, et al., "Determinants for the enhanced thermostability of hybrid (1-3,1-4)-β-glucanases", Eur. J. Biochem., vol. 216, pp. 829-834, 1993.
Tsai, et al., "Crystal Structure of Truncated *Fibrobacter succinogenes* 1,3-1,4-β-D Glucanase in Complex with β-1,3-1,4-Cellotriose", JMB, vol. 354, pp. 642-651, 2005.
Tsai, et al., "Structural basis for the inhibition of 1,3-1,4-β-D-glucanase by noncompetitive calcium ion and competitive Tris inhibitors", Biochemical and Biophysical Research Communications, vol. 407, pp. 593-598, 2011.

* cited by examiner

*Primary Examiner* — Nashaat Nashed
(74) *Attorney, Agent, or Firm* — Cesari and McKenna LLP

(57) ABSTRACT

Described herein is a fusion polypeptide that contains (a) a first segment containing a *Fibrobacter succinogenes* 1,3-1,4-β-D-glucanase (Fsβ-glucanase) or a fragment thereof; (b) a second segment containing a first *Thermotoga maritima* 1,3-β-D-glucanase (TmLam) or a fragment thereof; and (c) an optional third segment containing a second *Thermotoga maritima* 1,3-β-D-glucanase (TmLam) or a fragment thereof; wherein the fusion polypeptide has a glucanase activity. Also described are a nucleic acid molecule encoding the fusion polypeptide and a method of using the polypeptide.

5 Claims, 7 Drawing Sheets

DUAL-FUNCTIONAL HYBRID GLUCANASES

CROSS-REFERENCE TO RELATED APPLICATION

This application claims priority to U.S. Provisional Application No. 61/789,804, filed on Mar. 15, 2013, the content of which is hereby incorporated herein in its entirety.

BACKGROUND

Endo-β-D-glucanases are fibrolytic enzymes that play an important role in the hydrolysis of polysaccharide components. Several industrial applications of glucanase enzymes have been reported. For instance, 1,3-1,4-β-D-glucanases (EC 3.2.1.73, lichenase) can be used in the brewing industry and in the animal feeds industry. 1,3-β-D-Glucanases (laminarinases) have potential for use in commercial yeast extract production and for the conversion of algal biomass to fermentable sugars in the generation of bioenergy. The enzymes also have antimycotic activity for disease protection in plants.

SUMMARY

Described herein is a fusion polypeptide that includes (a) a first segment containing a *Fibrobacter succinogenes* 1,3-1,4-β-D-glucanase (Fsβ-glucanase) or a fragment thereof; (b) a second segment containing a first *Thermotoga maritima* 1,3-β-D-glucanase (TmLam, e.g., SEQ ID NO:1) or a fragment thereof; and (c) an optional third segment containing a second *Thermotoga maritima* 1,3-β-D-glucanase (TmLam, e.g., SEQ ID NO:1) or a fragment thereof; wherein the fusion polypeptide has a glucanase activity. For example, the first segment can contain $TFS_{W203F}$ (e.g., residues 1-248 of SEQ ID NO:3), the second segment and the optional third segment can each contain a first carbohydrate binding module of TmLam (CBM1, e.g., residues 19-176 of SEQ ID NO:1), a second carbohydrate binding module of TmLam (CBM2, e.g., residues 495-642 of SEQ ID NO:1), or a catalytic domain (CD) of TmLam (e.g., residues 211-488 of SEQ ID NO:1). In one embodiment, the fusion polypeptide can have an amino acid sequence that is at least 90% identical to the amino acid sequence of SEQ ID NO:5, 7, 9, 11, or 13.

Also described herein is an isolated nucleic acid molecule that has a nucleic acid sequence encoding the above-described fusion polypeptide. An expression vector containing the nucleic acid molecule and a host cell harboring the expression vector are also described.

The fusion polypeptide, which has glucanase activity, can be used to degrade a substrate, e.g., lichenin and larmarine.

The details of one or more embodiments are set forth in the accompanying drawing and the description below. Other features, objects, and advantages will be apparent from the description and drawing, and from the claims.

DETAILED DESCRIPTION

Figure 1:
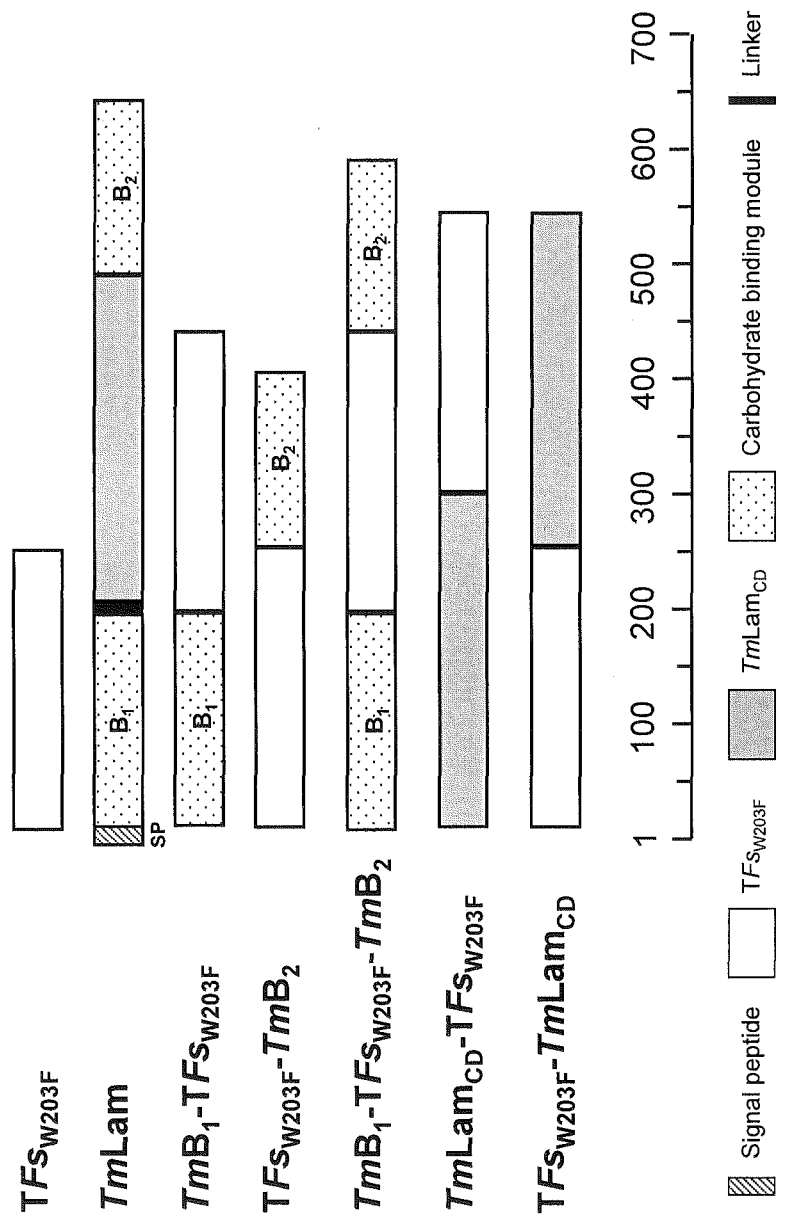
FIG. 1. is a schematic representation showing the structures of TmLam (e.g., SEQ ID NO:1), $TFs_{W203F}$ (having residues 1-248 of SEQ ID NO:3), and the hybrid glucanases described herein. The scale of the figure indicates amino acid residues.

Described herein are fusion polypeptides each containing at least a *Fibrobacter succinogenes* 1,3-1,4-β-D-glucanase (Fsβ-glucanase) or fragment thereof, and at least a *Thermotoga maritima* 1,3-β-D-glucanase (TmLam, e.g., SEQ ID NO:1) or a fragment thereof. The fusion polypeptides exhibit dual substrate specificities toward lichenin and larmarine, and also increased catalytic efficiencies and thermotolerance as compared to the parental single domain enzymes.

Shown below are a TmLam amino acid sequence and a TmLam nucleic acid sequence.

```
TmLam amino acid sequence (SEQ ID NO: 1)
catalytic domain TmLam_CD - residues 211-488; bold black
carbohydrate binding module (CBM) TmB_1 - residues 19-176, highlighted in grey
``` carbohydrate binding module (CBM) TmB₂ - residues 495-642, highlighted in grey
linkers - residues 177-210 and 489-494; underlined
signal peptide SP - residues 1-18

MMSRLVFALL LFPVFILAQN ILGNASFDEP ILIAGVDIDP PAEDGSIDTG GNWVFFTNSN

GEGTARVENG VLVVEITNGG DHTWSVQIIQ APIRVEKLHK YRVSFRAKAS SQKNIGVKIG

GTAGRGWTAY NPGTDESGGM VFELGTDWQK YEFEFVMRQE TDENARFEPQ LGRYTGTVWI

DDVVMEDIGV LEVSGEENEI YTEEDEDKVE DWQLVWSQEF DDGVIDPNIW NFEIGNGHAK

GIPGWGNGEL EYYTDENAFV ENGCLVIEAR KEQVSDEYGT YDYTSARMTT EGKFEIKYGK

IEIRAKLPKG KGIWPALWML GNNIGEVGWP TCGEIDIMEM LGHDTRTVYG TAHGPGYSGG

ASIGVAYHLP EGVPDFSEDF HIFSIEWDED EVEWYVDGQL YHVLSKDELA ELGLEWVFDH

PFFLILNVAV GGYWPGYPDE TTQFPQRMYI DYIRVYKDMN PETITGEVDD CEYEQAQQQA

GPEVTYEQIN NGTFDEPIVN DQANNPDEWF IWQAGDYGIS GARVSDYGVR DGYAYITIAD

PGTDTWHIQF NQWIGLYRGK TYTISFKAKA DTPRPINVKI LQNHDPWTNY FAQTVNLTAD

WQTFTFTYTH PDDADEVVQI SFELGEGTAT TIYFDDVTVS PQ

TmLam nucleic acid sequence (SEQ ID NO: 2)
GATGGCCATGGCTCAAAACATCCTTGGCAACGCTTCTTTCGATGAACCAATTCTCATCGCAGGTGTGGATATAGACC

CACCCGCAGAGGATGGCTCTATAGACACAGGAGGAAACTGGGTATTCTTCACCAATTCAAACGGTGAGGGAACGGCT

CGAGTCGAAAACGGCGTTCTCGTGGTTGAGATAACAAACGGAGGAGATCACACCTGGTCGGTTCAGATCATACAGGC

TCCCATACGTGTTGAGAAACTCCACAAGTACAGAGTTTCTTTCCGAGCCAAGGCTTCCTCTCAAAAGAACATCGGGG

TGAAGATAGGAGGAACGGCCGGAAGAGGATGGACCGCGTACAACCCCGGTACCGACGAATCCGGCGGCATGGTCTTC

GAGCTCGGAACAGATTGGCAGAAGTACGAGTTCGAATTCGTCATGAGACAGGAGACCGATGAAAATGCTCGTTTCGA

GTTTCAGCTTGGAAGGTATACCGGCACGGTCTGGATAGACGACGTAGTGATGGAGGACATCGGTGTTCTCGAGGTAA

GCGGTGAGGAAAACGAAATCTACACCGAGGAGGATGAAGACAAAGTGGAAGACTGGCAGCTCGTTTGGAGTCAGGAG

TTCGATGACGGTGTTATCGATCCGAACATCTGGAACTTCGAGATAGGAAACGGTCATGCAAAAGGTATTCCAGGCTG

GGGTAACGGGGAACTCGAGTACTATACAGACGAAAACGCGTTCGTTGAGAACGGCTGTCTTGTGATTGAGGCAAGAA

AAGAACAGGTTTCCGATGAGTACGGAACCTACGACTACACCTCAGCCAGGATGACCACAGAAGGAAAATTCGAAATA

AAGTACGGAAAAATCGAAATAAGGGCAAAACTTCCAAAAGGAAAAGGTATCTGGCCCGCTCTCTGGATGCTCGGAAA

CAACATAGGAGAGGTCGGATGGCCCACCTGTGGTGAGATAGACATCATGGAAATGCTTGGCCACGACACCAGAACCG

TTTATGGAACAGCACACGGTCCGGGATATTCTGGTGGTGCGAGTATAGGTGTTGCCTATCATCTTCCAGAAGGAGTT

CCTGATTTCTCCGAAGACTTCCACATTTTCTCCATCGAGTGGGACGAAGACGAAGTGGAGTGGTACGTGGACGGACA

GCTCTACCACGTCCTCAGCAAGGATGAACTGGCCGAACTCGGTCTTGAGTGGGTTTTCGACCATCCGTTCTTCCTCA

TTCTGAACGTTGCCGTGGGAGGCTACTGGCCGGGTTATCCCGACGAAACCACCCAATTCCCGCAGAGAATGTACATC

GACTACATCAGAGTCTATAAAGATATGAATCCGGAAACAATCACCGGGGAAGTGGATGACTGCGAATATGAACAAGC

ACAGCAGCAGGCAGGTCCCGAGGTGACCTATGAACAGATAAATAACGGCACTTTCGACGAACCTATTGTGAACGATC

AGGCCAACAACCCGGACGAATGGTTCATTTGGCAGGCGGGAGATTACGGGATCAGCGGTGCCAGGGTCTCCGATTAC

GGTGTCAGGGATGGCTACGCTTATATCACGATAGCCGATCCTGGAACTGACACGTGGCATATTCAGTTCAACCAGTG

GATAGGTCTTTACAGAGGAAAAACCTACACCATTTCTTTCAAAGCAAAAGCGGATACACCAAGACCTATAAATGTGA

AAATTCTGCAGAATCACGATCCCTGGACCAACTATTTTGCTCAAACGGTGAATCTCACAGCGGACTGGCAGACGTTC

ACGTTCACCTACACGCATCCAGACGATGCGGATGAGGTCGTTCAGATCAGTTTCGAACTCGGAGAAGGAACGGCAAC

TACGATTTATTTCGATGATGTCACGGTGAGCCCTCAAGCGGCCGCACTCGAGCACCACCACCACCACCACTGA

Fsβ-glucanases and variants thereof (e.g., TFs$_{SW203F}$ having the sequence of SEQ ID NO:3) are known in the art. See, e.g., U.S. Pat. No. 7,527,958. The amino acid sequence and nucleic acid sequence of TF$_{SW203F}$ are shown below. The amino acid sequence shown includes an optional C-terminal tag sequence (underlined).

TFsw2o3F amino
acid sequence  (SEQ ID NO: 3)
M V S A K D F S G A E L Y T L E E V Q Y G K F E A

R M K M A A A S G T V S S M F L Y Q N G S E I A D

G R P W V E V D I E V L G K N P G S F Q S N I I T

G K A G A Q K T S E K H H A V S P A A D Q A F H T

Y G L E W T P N Y V R W T V D G Q E V R K T E G G

Q V S N L T G T Q G L R F N L W S S E S A A W V G

Q F D E S K L P L F Q F I N W V K V Y K Y T P G Q

G E G G S D F T L D W T D N F D T F D G S R W G K

G D F T F D G N R V D L T D K N I Y S R D G M L I

L A L T R K G Q E S F N G Q V P R D D E P A P <u>N S</u>

<u>S S V D K L A A A L E H H H H H H</u>

TFsw2o3F nucleic
acid sequence  (SEQ ID NO: 4)
ATGGTTAGCGCAAAGGATTTTAGCGGTGCCGAACTCTACACGTTAGAAGA

AGTTCAGTACGGTAAGTTTGAAGCCCGTATGAAGATGGCAGCCGCATCGG

GAACAGTCAGTTCCATGTTCCTCTACCAGAATGGTTCCGAAATCGCCGAT

GGAAGGCCCTGGGTAGAAGTGGATATTGAAGTTCTCGGCAAGAATCCGG

CAGTTTCCAGTCCAACATCATTACCGGTAAGGCCGGCGCACAAAAGACTA

GCGAAAAGCACCATGCTGTTAGCCCCGCCGCCGATCAGGCTTTCCACACC

TACGGTCTCGAATGGACTCCGAATTACGTCCGCTGGACTGTTGACGGTCA

GGAAGTCCGCAAGACGGAAGGTGGCCAGGTTTCCAACTTGACAGGTACAC

AGGGACTCCGTTTTAACCTTTGGTCGTCTGAGAGTGCGGCTTGGGTTGGC

CAGTTCGATGAATCAAAGCTTCCGCTTTTCCAGTTCATCAACTGGGTCAA

GGTTTATAAGTATACGCCCGGCCAGGGCGAAGGCGGCAGCGACTTTACGC

TTGACTGGACCGACAATTTTGACACGTTTGATGGCTCCCGCTGGGGCAAG

GGTGACTTCACATTTGACGGTAACCGTGTCGACCTCACCGACAAGAACAT

CTACTCCAGAGATGGCATGTTGATCCTCGCCCTCACCCGCAAAGGTCAGG

AAAGCTTCAACGGCCAGGTTCCGAGAGATGACGAACCTGCTCCGAATTCG

AGCTCCGTCGACAAGCTTGCGGCCGCACTCGAGCACCACCACCACCACCA

CTGA

For example, the N-terminal CBM domain TmB$_1$ (e.g., residues 19-176 of SEQ ID NO:1), the catalytic domain TmLam$_{CD}$ (e.g., residues 211-488 of SEQ ID NO:1), and the C-terminal CBM domain TmB$_2$ of TmLam (e.g., residues 495-642 of SEQ ID NO:1), and TF$_{SW203F}$ (residues 1-248 of SEQ ID NO:3) can be combined in different configurations to generate novel fusion proteins. The various segments of the fusion polypeptides can be linked directly to each other or indirectly via a linker (e.g., a peptide including 1 to 100 amino acids).

The amino acid sequences and nucleic acid sequences of exemplary fusion polypeptides are shown below. Each amino acid sequence shown includes an optional C-terminal tag sequence (underlined).

TmLamCD-TFsw2o3F amino
acid sequence  (SEQ ID NO: 5)
M E D E D K V E D W Q L V W S Q E F D D G V I D P

N I W N F E I G N H A K G I P G W G N G E L E Y

Y T D E N A F V E N G C L V I E A R K E Q V S D E

Y G T Y D Y T S A R M T T E G K F E I K Y G K I E

I R A K L P K G K G I W P A L W M L G N N I G E V

G W P T C G E I D I M E M L G H D T R T V Y G T A

H G P G Y S G G A S I G V A Y H L P E G V P D F S

E D F H I F S I E W D E D E V E W Y V D G Q L Y H

V L S K D E L A E L G L E W V F D H P F F L I L N

V A V G G Y W P G Y P D E T T Q F P Q R M Y I D Y

I R V Y K D M N P E T I T G E V D D C E Y E Q A Q

Q Q A G P E V T Y E Q I N N A M V S A K D F S G A

E L Y T L E E V Q Y G K F E A R M K M A A A S G T

V S S M F L Y Q N G S E I A D G R P W V E V D I E

V L G K N P G S F Q S N I I T G K A G A Q K T S E

K H H A V S P A A D Q A F H T Y G L E W T P N Y V

R W T V D G Q E V R K T E G G Q V S N L T G T Q G

L R F N L W S S E S A A W V G Q F D E S K L P L F

Q F I N W V K V Y K Y T P G Q G E G G S D F T L D

W T D N F D T F D G S R W G K G D F T F D G N R V

D L T D K N I Y S R D G M L I L A L T R K G Q E S

F N G Q V P R D D E P A P <u>N S S S V D K L A A A L</u>

<u>E H H H H H H</u>

TmLamCD-TFsw2o3F nucleic
acid sequence  (SEQ ID NO: 6)
ATGGCCATGGAGGATGAAGACAAAGTGGAAGACTGGCAGCTCGTTTGGAG

TCAGGAGTTCGATGACGGTGTTATCGATCCGAACATCTGGAACTTCGAGA

TAGGAAACGGTCATGCAAAAGGTATTCCAGGCTGGGGTAACGGGAACTC

GAGTACTATACAGACGAAAACGCGTTCGTTGAGAACGGCTGTCTTGTGAT

TGAGGCAAGAAAAGAACAGGTTTCCGATGAGTACGGAACCTACGACTACA

CCTCAGCCAGGATGACCACAGAAGGAAAATTCGAAATAAAGTACGGAAAA

ATCGAAATAAGGGCAAAACTTCCAAAAGGAAAAGGTATCTGGCCCGCTCT

CTGGATGCTCGGAAACAACATAGGAGAGGTCGGATGGCCCACCTGTGGTG

AGATAGACATCATGGAAATGCTTGGCCACGACACCAGAACCGTTTATGGA

ACAGCACACGGTCCGGGATATTCTGGTGGTGCGAGTATAGGTGTTGCCTA

TCATCTTCCAGAAGGAGTTCCTGATTTCTCCGAAGACTTCCACATTTTCT

CCATCGAGTGGACGAAGACGAAGTGGAGTGGTACGTGGACGGACAGCTC

TACCACGTCCTCAGCAAGGATGAACTGGCCGAACTCGGTCTTGAGTGGGT

-continued

TTTCGACCATCCGTTCTTCCTCATTCTGAACGTTGCCGTGGGAGGCTACT

GGCCGGTTATCCCGACGAAACCACCCAATTCCCGCAGAGAATGTACATC

GACTACATCAGAGTCTATAAAGATATGAATCCGGAAACAATCACCGGGA

AGTGGATGACTGCGAATATGAACAAGCACAGCAGCAGGCAGGTCCCGAGG

TGACCTATGAACAGATAAATAACGCCATGGTTAGCGCAAAGGATTTTAGC

GGTGCCGAACTCTACACGTTAGAAGAAGTTCAGTACGGTAAGTTTGAAGC

CCGTATGAAGATGGCAGCCGCATCGGAACAGTCAGTTCCATGTTCCTCT

ACCAGAATGGTTCCGAAATCGCCGATGGAAGGCCCTGGTAGAAGTGGAT

ATTGAAGTTCTCGGCAAGAATCCGGCAGTTTCCAGTCCAACATCATTAC

CGGTAAGGCCGGCGCACAAAAGACTAGCGAAAAGCACCATGCTGTTAGCC

CCGCCGCCGATCAGGCTTTCCACACCTACGGTCTCGAATGGACTCCGAAT

TACGTCCGCTGGACTCTTGACGGTCAGGAAGTCCGCAAGACGGAAGGTGG

CCAGGTTTCCAACTTGACAGGTACACAGGGACTCCGTTTTAACCTTTGGT

CGTCTGAGAGTGCGGCTTGGGTTGGCCAGTTCGATGAATCAAAGCTTCCG

CTTTTCCAGTTCATCAACTCGGTCAAGGTTTATAAGTATACGCCGGCCA

GGGCGAAGGCGGCAGCGACTTTACGCTTGACTGGACCGACAATTTTGACA

CGTTTGATGGCTCCCGCTGGGCAAGGGTGACTTCACATTTGACGGTAAC

CGTGTCGACCTCACCGACAAGAACATCTACTCCAGAGATGGCATGTTGAT

CCTCGCCCTCACCCGCAAAGGTCAGGAAAGCTTCAACGGCCAGGTTCCGA

GAGATGACGAACCTGCCCCGAATTCGAGCTCCGTCGACAAGCTTGCGGCC

GCACTCGAGCACCACCACCACCACCACTGAGATCCGGCTGCTAACAAAGC

CCGAAAGAAGCTGAAGTTCTCGGT

TFsw2o3F-TmB2 amino
acid sequence (SEQ ID NO: 7)
M V S A K D F S G A E L Y T L E E V Q Y G K F E A
R M K M A A A S G T V S S M F L Y Q N G S E I A D
G R P W V E V D I E V L G K N P G S F Q S N I I T
G K A G A Q K T S E K H H A V S P A A D Q A F H T
Y G L E W T P N Y V R W T V D G Q E V R K T E G G
Q V S N L T G T Q G L R F N L W S S E S A A W V G
Q F D E S K L P L F Q F I N W V K V Y K Y T P G Q
G E G G S D F T L D W T D N F D T F D G S R W G K
G D F T F D G N R V D L T D K N I Y S R D G M L I
L A L T R K G Q E S F N G Q V P R D D E P A P N S
G T F D E P I V N D Q A N N P D E W F I W Q A G D
Y G I S G A R V S D Y G V R D G Y A Y I T I A D P
G T D T W H I Q F N Q W I G L Y R G K T Y T I S F
K A K A D T P R P I N V K I L Q N H D P W T N Y F
A Q T V N L T A D W Q T F T F T Y T H P D D A D E
V V Q I S F E L G E G T A T T I Y F D D V T V S P
Q A A A L E H H H H H H TFsw2o3F-TmB2 nucleic
acid sequence (SEQ ID NO: 8)
CCCCTTTTTAAAGGGCACATTCCCCTCTAGAATAATTTTGTTTAACTTTA

AGAAGGAGATATACATATGAAATACCTGCTGCCGACCGCTGCTGCTGGTC

TGCTGCTCCTCGCTGCCCAGCCGGCGATGGCCATGGTTAGCGCAAAGGAT

TTTAGCGGTGCCGAACTCTACACGTTAGAAGAAGTTCAGTACGGTAAGTT

TGAAGCCCGTATGAAGATGGCAGCCGCATCGGGAACAGTCAGTTCCATGT

TCCTCTACCAGAATGGTTCCGAAATCGCCGATGGAAGGCCCTGGTAGAA

GTGGATATTGAAGTTCTCGGCAAGAATCCGGCAGTTTCCAGTCCAACAT

CATTACCGGTAAGGCCGGCGCACAAAAGACTAGCGAAAAGCACCATGCTG

TTAGCCCCGCCGCCGATCAGGCTTTCCACACCTACGGTCTCGAATGGACT

CCGAATTACGTCCGCTGGACTGTTGACGGTCAGGAAGTCCGCAAGACGGA

AGGTGGCCAGGTTTCCAACTTGACAGGTACACAGGGACTCCGTTTTAACC

TTTGGTCGTCTGAGAGTGCGGCTTGGGTTGGCCAGTTCGATGAATCAAAG

CTTCCGCTTTTCCAGTTCATCAACTCGGTCAAGGTTTATAAGTATACGCC

GGGCCAGGGCGAAGGCGGCAGCGACTTTACGCTTGACTGGACCGACAATT

TTGACACGTTTGATGGCTCCCGCTGGGCAAGGGTGACTTCACATTTGAC

GGTAACCGTGTCGACCTCACCGACAAGAACATCTACTCCAGAGATGGCAT

GTTGATCCTCGCCCTCACCCGCAAAGGTCAGGAAAGCTTCAACGGCCAGG

TTCCGAGAGATGACGAACCTGCCCCGAATTCCGGCACTTTCGACGAACCT

ATTGTGAACGATCAGGCCAACAACCCGGACGAATGGTTCATTTGGCAGGC

GGGAGATTACGGGATCAGCGGTGCCAGGGTCTCCGATTACGGTGTCAGGG

ATGGCTACGCTTATATCACGATAGCCGATCCTGGAACTGACACGTGGCAT

ATTCAGTTCAACCAGTGGATAGGTCTTTACAGAGGAAAAACCTACACCAT

TTCTTTCAAAGCAAAAGCGGATACACCAAGACCTATAAATGTGAAAATTC

TGCAGAATCACGATCCCTGGACCAACTATTTTGCTCAAACGGTGAATCTC

ACAGCGGACTGGCAGACGTTCACGTTCACCTACACGCATCCAGACGATGC

GGATGAGGTCGTTCAGATCAGTTTCGAACTCGGAGAAGGAACGGCAACTA

CGATTTATTTCGATGATGTCACGGTGAGCCCTCAAGCGGCCGCACTCGAG

CACCACCACCACCACCACTGA

TFsw2o3F-TmLamcD amino
acid sequence (SEQ ID NO: 9)
M V S A K D F S G A E L Y T L E E V Q Y G K F E A
R M K M A A A S G T V S S M F L Y Q N G S E I A D
G R P W V E V D I E V L G K N P G S F Q S N I I T
G K A G A Q K T S E K H H A V S P A A D Q A F H T
Y G L E W T P N Y V R W T V D G Q E V R K T E G G
Q V S N L T G T Q G L R F N L W S S E S A A W V G
Q F D E S K L P L F Q F I N W V K V Y K Y T P G Q
G E G G S D F T L D W T D N F D T F D G S R W G K
G D F T F D G N R V D L T D K N I Y S R D G M L I
L A L T R K G Q E S F N G Q V P R D D E P A P N S
E D W Q L V W S Q E F D D G V I D P N I W N F E I GNGHAKGIPGWGNGELEYYTDENAF
VENGCLVIEARKEQVSDEYGTYDYT
SARMTTEGKFEIKYGKIEIRAKLPK
GKGIWPALWMLGNNIGEVGWPTCGE
IDIMEMLGHDTRTVYGTAHGPGYSG
GASIGVAYHLPEGVPDFSEDFHIFS
IEWDEDEVEWYVDGQLYHVLSKDEL
AELGLEWVFDHPFFLILNVAVGGYW
PGYPDETTQFPQRMYIDYIRVYKDM
NPETITGEVDDCEYEQAQQQAGPEV
TYEQINN<u>AAALEHHHHHH</u>

TFsw2o3F-TmLamcD nucleic
acid sequence (SEQ ID NO: 10)
GAATGGATAACGGAAATTCCCTCTAGAATAATTTTGTTTAACTTTAAGA
AGGAGATATACATATGAAATACCTGCTGGCGACCGCTGCTGCTGGTCTGC
TGCTCCTCGCTGCCCAGCCGGCGATGGCCATGGTTAGCGCAAAGGATTTT
AGCGGTGCCGAACTCTACACGTTAGAAGAAGTTCAGTACGGTAAGTTTGA
AGCCCGTATGAAGATGGCAGCCGCATCGGAACAGTCAGTTCCATCTTCC
TCTACCAGAATGGTTCCGAAATCGCCGATGGAAGGCCCTGGTAGAAGTG
GATATTGAAGTTCTCGGCAAGAATCCGGCAGTTTCCAGTCCAACATCAT
TACCGGTAAGGCCGGCGCACAAAAGACTAGCGAAAAGCACCATGCTGTTA
GCCCCGCCGCCGATCAGGCTTTCCACACCTACGCTCTCGAATGGACTCCG
AATTACGTCCGCTGGACTGTTGACGCTCAGGAAGTCCGCAAGACGGAAGG
TGGCCAGGTTTCCAACTTGACAGGTACACAGGGACTCCGTTTTAACCTTT
GGTCGTCTGAGAGTGCGGCTTGGGTTGGCCAGTTCGATGAATCAAAGCTT
CCGCTTTTCCAGTTCATCAACTGGGTCAAGGTTTATAAGTATACGCCGG
CCAGGGCGAAGGCGGCAGCGACTTTACGCTTGACTGGACCGACAATTTTG
ACACGTTTGATGGCTCCCGCTGGGCAAGGGTGACTTCACATTTGACGGT
AACCGTGTCGACCTCACCGACAAGAACATCTACTCCAGAGATGGCATGTT
GATCCTCGCCCTCACCCGCAAAGGTCAAGAAAGCTTCAACGGCCAGGTTC
CGAGAGATGACGAACCTGCTCCGAATTCGGAAGACTGGCAGCTCGTTTGG
AGTCAGGAGTTCGATGACGGTCTTATCGATCCGAACATCTGGAACTTCGA
GATAGGAAACGCTCATGCAAAAGGTATTCCAGGCTGGGGTAACGCGGAAC
TCGAGTACTATACAGACGAAAACGCGTTCGTTGAGAACGGCTGTCTTGTG
ATTGAGGCAAGAAAGAACAGGTTTCCGATGAGTACGGAACCTACGACTA
CACCTCAGCCAGGATGACCACAGAAGGAAAATTCGAAATAAAGTACGGAA
AAATCGAAATAAGGGCAAACTTCCAAAAGGAAAAGGTATCTGGCCCGCT
CTCTGGATGCTCGGAAACAACATAGGAGAGGTCGGATGGCCCACCTGTGG
TGAGATAGACATCATGGAAATGCTTGGCCACGACACCAGAACCGTTTATG
GAACAGCACACGCTCCGGATATTCTGGTGGTGCGAGTATAGGTGTTGCC
TATCATCTTCCAGAAGGAGTTCCTGATTTCTCCGAAGACTTCCACATTTT CTCCATCGAGTGGACGAAGACGAAGTGGAGTGGTACGTGGACGGACAGC
TCTACCACGTCCTCAGCAAGGATGAACTGGCCGAACTCGGTCTTGAGTGG
GTTTTCGACCATCCGTTCTTCCTCATTCTGAACGTTGCCGTGGGAGGCTA
CTGGCCGGGTTATCCCGACGAAACCACCCAATTCCCGCAGAGAATGTACA
TCGACTACATCAGAGTCTATAAAGATATGAATCCGGAAACAATCACCGGG
GAAGTGGATGACTGCGAATATGAACAAGCACAGCAGCAGGCAGGTCCCGA
GGTGACCTATGAACAGATAAATAACGCGGCCGCACTCGAGCACCACCACC
ACCACCACTGAGATCCGGCTGCTAACAAAGCCCGAAAGAAGCTAAGTGCG
GGAA Tins 1-TFSW203F- TMB2 amino
acid sequence (SEQ ID NO: 11)
MAQNILGNASFDEPILIAGVDIDPP
AEDGSIDTGGNWVFFTNSNGEGTAR
VENGVLVVEITNGGDHTWSVQIIQA
PIRVEKLHKYRVSFRAKASSQKNIG
VKIGGTAGRGWTAYNPGTDESGGMV
FELGTDWQKYEFEFVMRQETDENAR
FEFQLGRYTGTVWIDDVVMEDIGVL
EVSGEENEIYTMVSAKDFSGAELYT
LEEVQYGKFEARMKMAAASGTVSSM
FLYQNGSEIADGRPWVEVDIEVLGK
NPGSFQSNIITGKAGAQKTSEKHHA
VSPAADQAFHTYGLEWTPNYVRWTV
DGQEVRKTEGGQVSNLTGTQGLRFN
LWSSESAAWVGQFDESKLPLFQFIN
WVKVYKYTPGQGEGGSDFTLDWTDN
FDTFDGSRWGKGDFTFDGNRVDLTD
KNIYSRDGMLILALTRKGQESFNGQ
VPRDDEPAPNSGTFDEPIVNDQANN
PDEWFIWQAGDYGISGARVSDYGVR
DGYAYITIADPGTDTWHIQFNQWIG
LYRGKTYTISFKAKADTPRPINVKI
LQNHDPWTNYFAQTVNLTADWQTFT
FTYTHPDDADEVVQISFELGEGTAT
TIYFDDVTVSPQ<u>AAALEHHHHHH</u>

Tms 1-TFSW203F- TMB2 amino
acid sequence (SEQ ID NO: 12)
CGCTCTATACCCGAAAAATTTCCCTTCTAGACTAATTTTGTTTAACTTT
AAGAAGGAGATATACATATGAAATACCTGCTGCCGACCGCTGCTGCTGGT
CTGCTGCTCCTCGCTGCCCAGCCGGCGATGGCCATGGCTCAAAACATCCT
TGGCAACGCTTCTTTCGATGAACCAATTCTCATCGCAGGTGTGGATATAG
ACCCACCCGCAGAGGATGGCTCTATAGACACAGGAGGAAACTGGGTATTC
TTCACCAATTCAAACGGTGAGGGAACGGCTCGAGTCGAAAACGGCGTTCT

```
CGTGGTTGAGATAACAAACGGAGGAGATCACACCTGGTCGGTTCAGATCA

TACAGGCTCCCATACGTGTTGAGAAACTCCACAAGTACAGAGTTTCTTTC

CGAGCCAAGGCTTCCTCTCAAAAGAACATCGGGGTGAAGATAGGAGGAAC

GGCCGGAAGAGGATGGACCGCGTACAACCCCGGTACCGACGAATCCGGCG

GCATGGTCTTCGAGCTCGGAACAGATTGGCAGAAGTACGAGTTCGAATTC

GTCATGAGACAGGAGACCGATGAAAATGCTCGTTTCGAGTTTCAGCTTGG

AAGGTATACCGGCACGGTCTGGATAGACGACGTAGTGATGGAGGACATCG

GTGTTCTCGAGGTAAGCGGTGAGGAAAACGAAATCTACACCATGGTTAGC

GCAAAGGATTTTAGCGGTGCCGAACTCTACACGTTAGAAGAAGTTCAGTA

CGGTAAGTTTGAAGCCCGTATGAAGATGGCAGCCGCATCGGAACAGTCA

GTTCCATGTTCCTCTACCAGAATGGTTCCGAAATCGCCGATGGAAGGCCC

TGGTAGAAGTGGATATTGAAGTTCTCGGCAAGAATCCGGGCAGTTTCCA

GTCCAACATCATTACCGGTAAGGCCGGCGCACAAAAGACTAGCGAAAAGC

ACCATGCTGTTAGCCCCGCCGCCGATCAGGCTTTCCACACCTACGGTCTC

GAATGGACTCCGAATTACGTCCGCTGGACTGTTGACGGTCAGGAAGTCCG

CAAGACGGAAGGTGGCCAGGTTTCCAACTTGACAGGTACACAGGGACTCC

GTTTTAACCTTTGGTCGTCTGAGAGTGCGGCTTGGGTTGGCCAGTTCGAT

GAATCAAAGCTTCCGCTTTTCCAGTTCATCAACTGGGTCAAGGTTTATAA

GTATACGCCGGCCAGGGCGAAGGCGGCAGCGACTTTACGCTTGACTGGA

CCGACAATTTTGACACGTTTGATGGCTCCCGCTGGGCAAGGGTGACTTC

ACATTTGACGGTAACCGTGTCGACCTCACCGACAAGAACATCTACTCCAG

AGATGGCATGTTGATCCTCGCCCTCACCCGCAAAGGTCAGGAAAGCTTCA

ACGGCCAGGTTCCGAGAGATGACGAACCTGCCCCGAATTCCGGCACTTTC

GACGAACCTATTGTGAACGATCAGGCCAACAACCCGGACGAATGGTTCAT

TTGGCAGGCGGAGATTACGGGATCAGCGGTGCCAGGGTCTCCGATTACG

GTGTCAGGGATGGCTACGCTTATATCACGATAGCCGATCCTGGAACTGAC

ACGTGGCATATTCAGTTCAACCAGTGGATAGGTCTTTACAGAGGAAAAAC

CTACACCATTTCTTTCAAAGCAAAAGCGGATACACCAAGACCTATAAATG

TGAAAATTCTGCAGAATCACGATCCCTGGACCAACTATTTTGCTCAAACG

GTGAATCTCACAGCGGACTGGCAGACGTTCACGTTCACCTACACGCATCC

AGACGATGCGGATGAGGTCGTTCAGATCAGTTTCGAACTCGGAGAAGGAA

CGGCAACTACGATTTATTTCGATGATGTCACGGTGAGCCCTCAAGCGGCC

GCACTCGAGCACCACCACCACCACCACTGA
```

Tinsi-TFsw2o3F amino
acid sequence (SEQ ID NO: 13)
M A Q N I L G N A S F D E P I L I A G V D I D P P

A E D G S I D T G G N W V F F T N S N G E G T A R

V E N G V L V V E I T N G G D H T W S V Q I I Q A

P I R V E K L H K Y R V S F R A K A S S Q K N I G

V K I G G T A G R G W T A Y N P G T D E S G G M V

F E L G T D W Q K Y E F E F V M R Q E T D E N A R

F E F Q L G R Y T G T V W I D D V V M E D I G V L

E V S G E E N E I Y T M V S A K D F S G A E L Y T

L E E V Q Y G K F E A R M K M A A A S G T V S S M

F L Y Q N G S E I A D G R P W V E V D I E V L G K

N P G S F Q S N I I T G K A G A Q K T S E K H H A

V S P A A D Q A F H T Y G L E W T P N Y V R W T V

D G Q E V R K T E G G Q V S N L T G T Q G L R F N

L W S S E S A A W V G Q F D E S K L P L F Q F I N

W V K V Y K Y T P G Q G E G G S D F T L D W T D N

F D T F D G S R W G K G D F T F D G N R V D L T D

K N I Y S R D G M L I L A L T R K G Q E S F N G Q

V P R D D E P A P <u>N S S S V D K L A A A L E H H H</u>

<u>H H H</u>

Tinsi-TFsw2o3F nucleic
acid sequence (SEQ ID NO: 14)
```
TTTAAGAAGGAGATATACATATGAAATACCTCCTCCGACCGCTCCTCCT

GGTCTCCTCCTCCTCGCTCCCCAGCCGCGATGGCCATGGCTCAAAACAT

CCTTGGCAACGCTTCTTTCGATGAACCAATTCTCATCGCAGGTGTGGATA

TAGACCCACCCGCAGAGGATGGCTCTATAGACACAGGAGGAAACTGGTA

TTCTTCACCAATTCAAACGGTGAGGGAACGGCTCGAGTCGAAAACGGCGT

TCTCGTGGTTGAGATAACAAACGGAGGAGATCACACCTGGTCGGTTCAGA

TCATACAGGCTCCCATACGTGTTGAGAAACTCCACAAGTACAGAGTTTCT

TTCCGAGCCAAGGCTTCCTCTCAAAAGAACATCGGGGTGAAGATAGGAGG

AACGGCCGGAAGAGGATGGACCGCGTACAACCCCGGTACCGACGAATCCG

GCGGCATGGTCTTCGAGCTCGGAACAGATTGGCAGAAGTACGAGTTCGAA

TTCGTCATGAGACAGGAGACCGATGAAAATGCTCGTTTCGAGTTTCAGCT

TGGAAGGTATACCGGCACGGTCTGGATAGACGACGTAGTGATGGAGGACA

TCGGTGTTCTCGAGGTAAGCGGTGAGGAAAACGAAATCTACACCATGGTT

AGCGCAAAGGATTTTAGCGGTGCCGAACTCTACACGTTAGAAGAAGTTCA

GTACGGTAAGTTTGAAGCCCGTATGAAGATGGCAGCCGCATCGGAACAG

TCAGTTCCATGTTCCTCTACCAGAATGGTTCCGAAATCGCCGATGGAAGG

CCCTGGTAGAAGTGGATATTGAAGTTCTCGGCAAGAATCCGGGCAGTTT

CCAGTCCAACATCATTACCGGTAAGGCCGGCGCACAAAAGACTAGCGAAA

AGCACCATGCTGTTAGCCCCGCCGCCGATCAGGCTTTCCACACCTACGGT

CTCGAATGGACTCCGAATTACGTCCGCTGGACTGTTGACGGTCAGGAAGT

CCGCAAGACGGAAGGTGGCCAGGTTTCCAACTTGACAGGTACACAGGGAC

TCCGTTTTAACCTTTGGTCGTCTGAGAGTGCGGCTTGGGTTGGCCAGTTC

GATGAATCAAAGCTTCCGCTTTTCCAGTTCATCAACTGGGTCAAGGTTTA

TAAGTATACGCCGGCCAGGGCGAAGGCGGCAGCGACTTTACGCTTGACT

GGACCGACAATTTTGACACGTTTGATGGCTCCCGCTGGGCAAGGGTGAC

TTCACATTTGACGGTAACCGTGTCGACCTCACCGACAAGAACATCTACTC

CAGAGATGGCATGTTGATCCTCGCCCTCACCCGCAAAGGTCAGGAAAGCT
```

-continued

```
TCAACGCCCAGGTTCCGAGAGATGACGAACCTCCCCCGAATTCGAGCTCC

GTCGACAAGCTTGCGCCCGCACTCGAGCACCACCACCACCACCACTGAGA

TCCGGCTCCTAACAAAGCCCGAAAGAAGCTAGGGTTTTTCGTC
```

The fusion polypeptides and nucleic acid molecules described herein can be generated using methods known in the art, e.g., recombinant technology.

The nucleic acid molecules can be used to express the polypeptides and fusion polypeptides described herein. Each nucleic acid molecule can be linked to suitable regulatory sequences to generate an expression vector.

Examples of the vector include a plasmid, cosmid, or viral vector. The vector includes a nucleic acid in a form suitable for expression of the nucleic acid in a host cell. Preferably the vector includes one or more regulatory sequences operatively linked to the nucleic acid sequence to be expressed. A regulatory sequence includes promoters, enhancers, and other expression control elements (e.g., T7 promoter, cauliflower mosaic virus 35S promoter sequences or polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce the polypeptide or fusion protein of this invention.

Host cells include *E. coli* cells, insect cells (e.g., using baculovirus expression vectors), plant cells, yeast cells, and mammalian cells. See e.g., Goeddel, (1990) Gene Expression Technology: Methods in Enzymology 185, Academic Press, San Diego, Calif.

Host cells containing an expression vector for expressing a fusion polypeptide described herein can be cultured under conditions allowing expression of the polypeptide. The expressed polypeptide can then be isolated from the host cells or culture medium.

The isolated fusion polypeptide can be used for various purposes. Thus, described herein are also methods of using the fusion polypeptides. For example, the fusion polypeptide can be used to degrade a substrate, e.g., a polysaccharide. The fusion polypeptide can also be used in industrial applications.

The specific example below is to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are herein incorporated by reference in their entirety.

A truncated and mutated 1,3-1,4-β-D-glucanase gene (encoding TFs$_{W203F}$ having residues 1-248 of SEQ ID NO:3) from *Fibrobacter succinogenes*, and a 1,3-β-D-glucanase gene (encoding TmLam having the sequence of SEQ ID NO:1) from hyperthermophilic *Thermotoga maritima* were used to generate hybrid enzymes. The substrate binding domains (TmB$_1$ having residues 19-176 of SEQ ID NO:1 and TmB$_2$ having residues 495-642 of SEQ ID NO:1) and the catalytic domain (TmLam$_{CD}$ having residues 211-488 of SEQ ID NO:1) of TmLam (SEQ ID NO:1) were linked to the N- or C-terminus of TFs$_{W203F}$ (having residues 1-248 of SEQ ID NO:3) to create four hybrid enzymes, TmB$_1$-TFs$_{W203F}$ (having the sequence of SEQ ID NO:13 with or without the optional C-terminal taq), TFs$_{W203F}$-TmB$_2$ (having the sequence of SEQ ID NO:7 with or without the optional C-terminal taq), TmB$_1$-TFs$_{W203F}$-TmB$_2$ (having the sequence of SEQ ID NO:11 with or without the optional C-terminal taq), and TFs$_{W203F}$-TmLam$_{CD}$ (having the sequence of SEQ ID NO:9 with or without the optional C-terminal taq). The results obtained from kinetic studies show that increased specific activities and turnover rate for lichenan and laminarin were observed in TmB$_1$-TFs$_{W203F}$-TmB$_2$ (having the sequence of SEQ ID NO:11 with or without the optional C-terminal taq) and TFs$_{W203F}$-TmLam$_{CD}$ (having the sequence of SEQ ID NO:9 with or without the optional C-terminal taq), respectively. Furthermore, fluorescence and CD spectrometric analyses indicated that the hybrid TFs$_{W203F}$-TmLam$_{CD}$ (having the sequence of SEQ ID NO:9 with or without the optional C-terminal taq) was structurally more stable and more thermal tolerant than the parental TFs$_{W203F}$ (having residues 1-248 of SEQ ID NO:3).

Materials and Methods (1) Bacterial Strains and Cultivation

*Thermotoga maritima* MSB8 (Huber et al., 1986, Arch. Microbiol., 144, 324-333) was purchased from ATCC (DSM 3109) and used as the source for the cloning of the 1,3-β-D-glucanase (TmLam) gene. *T. maritima* cells were grown anaerobically at 70° C. in a growth medium (ATCC #2114 broth) composed of 25% artificial sea water (v/v) supplemented with the following components (g/L): soluble starch, 5.0; yeast extract, 0.5; NaCl, 20; KH$_2$PO$_4$, 0.5; NiCl$_2$.6H$_2$O, 0.002; Na$_2$S.9H$_2$O, 0.5; resazurin, 0.001; and Wolfe's mineral solution (1.5%, v/v). *E. coli* strain XL-1 Blue (Stratagene) was used for the purpose of cloning, and BL21(DE3) (Novagen) competent cells were employed for the overexpression of cloned genes. The conditions for cultivation of recombinant cells, media and overexpression were in accordance with previously-published methods (Wen et al., 2005, Biochemistry, 44, 9197-9205), and plasmid pET26b(+) was used for the cloning and expression of recombinant glucanase genes.

(2) Construction of Plasmids for Expression of Parental and Hybrid Glucanases

The chromosomal DNA of *T. maritima* was isolated from cultured cell using QIAGEN Genomic-tip 20/G (QIAGEN). The DNA was used as the template for PCR amplification of the open reading frame of TmLam gene (without the presence of N-terminal signal sequence) by a pair of specific primers TmNcoI and TmNotI. See Table 1. The amplified DNA fragments were digested with NcoI and NotI and then subcloned into pET26b(+) vector to form pTmLam.

(3) Construction of Recombinant Glucanase Genes

The TFs$_{W203F}$ plasmid (pTFs$_{W203F}$) previously created (Tsai et al., 2011, Biochem. Bioph. Res. Comm., 407, 593-598) was used to create hybrid enzymes with the CBM and catalytic domains of TmLam. The primers for the construction of hybrid glucanase genes are shown in Table 1.

TABLE 1

Oligonucleotide primers for the subcloning of specific protein domains in *T. maritima* 1,3-β-D-glucanase.

| Primer Name | SEQ ID NO | Sequence |
|---|---|---|
| TmNcoI | 15 | 5'-CCTGTTTTCACCATGGCTCAAAACATCCT TGGC-3' |

TABLE 1-continued

Oligonucleotide primers for the subcloning of specific protein domains in T. maritima 1,3-β-D-glucanase.

| Primer Name | SEQ ID NO | Sequence |
|---|---|---|
| TmNotI | 16 | 5'-GCACCGGGGATGCGGCCGCTTGAGGGCTC-3' |
| TmB$_1$(+)/ EcoRI | 17 | 5'-GGATGAAGAGAATCGGAAGACTGGC-3' |
| TmB$_1$(+)/ NcoI | 18 | 5'-CGAAATCTACACCATGGAGGATGAAGAC-3' |
| TmB$_1$(-)/ NcoI | 19 | 5'-GTCTTCATCCTCCATGGTGTAGATTTCG-3' |
| TmB$_2$(+)/ EcoRI | 20 | 5'-CCTATGAACAGATGAATTCCGGCACTTTCG-3' |
| TmB$_2$(-)/ HindIII | 21 | 5'-CGAAAGTGCCAAGCTTTATCTGTTCATAGG-3' |
| TmB$_2$(-)/ NcoI | 22 | 5'-CGACCATGGCGTTATTTATCTGTTCATAGG-3' |
| TmB$_2$(-)/ NotI | 23 | 5'-GCGGCCGCGTTATTATCTGTTCATAGG-3' |
| 5A$^a$ | 24 | 5'-AAATACCTGCTGCCGACCG-3' |
| 3B$^a$ | 25 | 5'-GCTAGTTATTGCTCAGCGGTG-3' |

$^a$Vector-specific primers

The DNA fragments of N-terminal CBM4-1 (TmB$_1$) and C-terminal CBM4-2 (TmB$_2$) from the TmLam gene were obtained by PCR amplification with specific primer pairs, 5A and TmB$_1$(-)/NcoI and TmB$_2$(+)/EcoRI and 3B, respectively. The amplified DNA products were digested with appropriate restriction enzymes and ligated into plasmids pTFs$_{W203F}$, before being pre-digested with the same restriction enzymes to obtain new chimera plasmids pTmB$_1$-TFs$_{W203F}$ and pTFs$_{W203F}$-TmB$_2$. Furthermore, the amplified TmB$_1$ DNA fragments and plasmid pTFs$_{W203F}$-TmB$_2$ were all pre-digested with NcoI and then ligated together to create another gene construct, pTmB$_1$-TFs$_{W203F}$-TmB$_2$. The chimera plasmids containing the catalytic domain of TmLam, pTmLam$_{CD}$ or the hybrid enzyme genes, pTFs$_{W203F}$-TmLam$_{CD}$ and pTmLam$_{CD}$-TFs$_{W203F}$, in other fibrolytic enzymes, were created and obtained using specific pairs of primers: TmB$_1$(+)/NcoI and TmB$_2$(-)/HindIII, TmB$_1$(+)/NcoI and TmB$_2$(-)/NcoI as well as TmB$_1$(+)/EcoRI and TmB$_2$(-)/NotI, respectively.

All of the created gene constructs were verified by the automated sequencing method through the use of the ABI Prism BigDye Terminator Cycle Sequencing Ready Reaction kit (Applied Biosystems). The confirmed plasmid genes were transformed into E. coli BL21(DE3) host cells for protein overexpression.

(4) Expression and Purification of Recombinant Proteins

E. coli BL21(DE3) cells harboring the appropriate plasmids were grown in two liters of LB medium containing kanamycin at 33° C. until the OD$_{600}$ reached 0.8-1.0. Protein expression was then induced by the addition of IPTG (0.6 mM) and the culture was allowed to shake at 28-30° C. for 16 hours. The supernatant, containing expressed proteins, was harvested from the culture medium, and PMSF (1 mM) and leupeptin (1 µg/ml) were added to avoid protein degradation. Subsequently, the supernatant was concentrated using a Pellicon™-2 Mini Cassette Holder with a Biomax™ 10K filter assembled on a Labscale™ TFF system (Millipore). The concentrate was dialyzed against sodium phosphate buffer (50 mM, pH 8.0) containing imidazole (10 mM) and NaCl (0.3 M) at 4° C., and the resulting solution was applied to a 1.5×20 cm column containing pre-equilibrated HIS-select™ nickel affinity gel (Sigma). The column was then washed with sodium phosphate buffer (50 mM, pH 8.0) containing imidazole (20 mM) and NaCl (0.3 M), followed with a five-times column volume of imidazole gradient (20-250 mM) in the same buffer, for protein elution. The fractions were analyzed by 12% SDS-PAGE, and the target proteins were pooled together for dialysis against sodium phosphate buffer (50 mM, pH 7.0) at 4° C. Purified proteins were stored in the presence of glycerol (10%) at −20° C., and protein concentration was determined by the Bradford method (Bio-Rad), using BSA (Sigma) as the standard.

(5) Kinetic Studies

The enzymatic activities of the purified parental or hybrid glucanases were measured by determining the rate of reducing sugar production from the hydrolysis of substrates, lichenan and laminarin (Sigma). The reduction of sugars was quantified by the use of 3,5-dinitrosalicylic acid (DNS) reagent (Wood and Bhat, 1988, Methods in Enzymology, Vol. 160, Academic Press, pp. 87-112) with glucose as the standard. A standard enzyme activity assay was performed in a 0.3 ml reaction mixture, as described previously (Cheng et al., 2002, Biochemistry, 41, 8759-8766). One unit of enzyme activity was defined as the amount of enzyme required to produce 1 µmol of reducing sugar (glucose equivalent) per minute, and the specific activity was expressed in µmol of glucose per minute per nmol of protein. Various amounts of purified enzymes were used in each kinetic assay reaction, depending on the enzymatic activity. The kinetic data was analyzed using either ENZFITTER (BIOSOFT).

(6) On Gel Substrate-Enzyme Binding Analysis

The substrate-binding capability of the single domain and hybrid glucanases was evaluated using affinity SDS-PAGE. Unheated protein samples in a lysis buffer, in which the enzymes were not denatured and remained active, were separated on a 12% SDS gel with or without the presence of 0.1% substrate lichenan, along with a set of molecular weight (MW) standards (PageRuler™ Prestained Protein Ladder 10-170-kDa, Fermentas) on the same gel. After electrophoresis, proteins were visualized by staining with Coomassie brilliant blue R-250. Rf$_0$ and Rf were defined as the ratio of the migration distance moved by each protein sample to the migration distance of the dye front on gel without and with substrate, respectively.

(7) Effects of Temperature on Parental and Hybrid Glucanases

Purified parental and hybrid glucanases were incubated individually for ten minutes at temperatures within the range of 30° C. and 80° C., at intervals of 5° C. Residual enzyme activity was determined immediately after heat treatment in sodium citrate buffer (50 mM, pH 6.0) at 45° C. using lichenan as the substrate (Cheng et al., 2002, Biochemistry, 41, 8759-8766).

(8) Fluorescence Spectrometry

The fluorescence emission spectra of TFs$_{W203F}$ (having residues 1-248 of SEQ ID NO:3) and TFs$_{W203F}$-TmLam$_{CD}$ (having the sequence of SEQ ID NO:9 with or without the optional C-terminal taq) were taken on an AMICO-Bowman Series 2 spectrometer (Spectronic Instruments) with a 10×10 mm quartz cuvette incubated at 20° C., 50° C. and 75° C., respectively. Emission spectra were recorded from 310 nm to 430 nm by excitation at 295 nm, with a 4-nm monochromator bandpass. A final protein concentration of 30 μm/ml in sodium phosphate buffer (50 mM, pH 7.0) was used for all assays. Glucanase samples denatured with urea (8 M), or urea-denatured and then renatured by dialysis against sodium phosphate buffer (50 mM, pH 7.0) at 4° C. for 24 hours, were also analyzed for their fluorescence emission spectra at 25° C. Each measurement was carried out in triplicate.

(9) Circular Dichroism (CD) Spectrometry

CD spectrometric studies on the $TFs_{W203F}$ (having residues 1-248 of SEQ ID NO:3) and $TFs_{W203F}$-$TmLam_{CD}$ (having the sequence of SEQ ID NO:9 with or without the optional C-terminal taq) proteins were carried out on a Jasco J715 CD spectrometer with a 10-mm cell at a range of temperatures from 30° C. to 90° C. Spectra were collected from 200 nm to 260 nm in 0.1 nm increments. Each spectrum was blank-collected and smoothed using a software package provided with the instruments.

(10) Protein Reactivation Assays

Purified $TFs_{W203F}$ (having residues 1-248 of SEQ ID NO:3) and $TFs_{W203F}$-$TmLam_{CD}$ (having the sequence of SEQ ID NO:9 with or without the optional C-terminal taq) enzymes (30 μg/ml) were pretreated at 90° C. for ten minutes and then transferred to room temperature (25° C.). Recovery of enzymatic activity and protein re-folding of the heat-treated proteins within a ten-minute time frame at room temperature were measured using standard enzyme activity assay and fluorescence spectrometry respectively.

(11) Structural Modeling

In order to facilitate the interpretation of the kinetic data of TFsW203F (having residues 1-248 of SEQ ID NO:3) and hybrid enzymes from a structural point of view, we created a protein model complexed with oligosaccharides using the 3D structures of TmB2 (1GUI_A), truncated Fsβ-glucanase, TFs (1ZM1_A) (Tsai et al., 2005, J. Mol. Biol., 354, 642-651), $TFs_{W203F}$ (3H0O_A) (Tsai et al., 2011, Biochem. Bioph. Res. Comm., 407, 593-598) and $TmLam_{CD}$ (3AZZ_A) (Jeng et al., 2011, J. Biol. Chem., 286, 45030-45040), along with a model of $TmB_1$ newly created for this study, the structure of which has not yet been resolved. The structural model of $TmB_1$ was generated by using the HHpred (Soding et al., 2005, Nucleic Acids Res., 33, W244-W248), a website for homology detection and structure prediction by HMM-HMM comparison, based on the top five templates with the highest scores (PDB accession code: 3K4Z_A, 1CX1_A, 3P6B_A, 1GU3_A and 1GUI_A). The secondary structure matching (SSM) algorithm, with default settings for multiple 3D alignment in the PDBeFold server (Krissinel and Henrick, 2004, Acta Crystallogr. D Biol. Crystallogr., 60, 2256-2268), was used to superimpose all protein structures. After this the proteins were docked with β-1,3-cellohexose (from 1GUI) or β-1,3-1,4-celloheptaose (modeled), which were generated and energy-minimized by Coot (Emsley and Cowtan, 2004, Acta Crystallogr. D Biol. Crystallogr., 60, 2126-2132) and REFMAC5 (Murshudov et al., 2011, Acta Crystallogr. D Biol. Crystallogr., 67, 355-367.) from the CCP4 program suite (Collaborative Computational Project, Number 4, 1994; Winn et al., 2011, Acta Crystallogr. D Biol. Crystallogr., 67, 235-242), with the β-1,3-1,4-cellotriose in 1ZM1 as the template. The structural figures were then produced using PyMOL (DeLano Scientific; world wide web at pymol.org).

Results (1) Construction and Purification of Hybrid Glucanases

Figure 2:
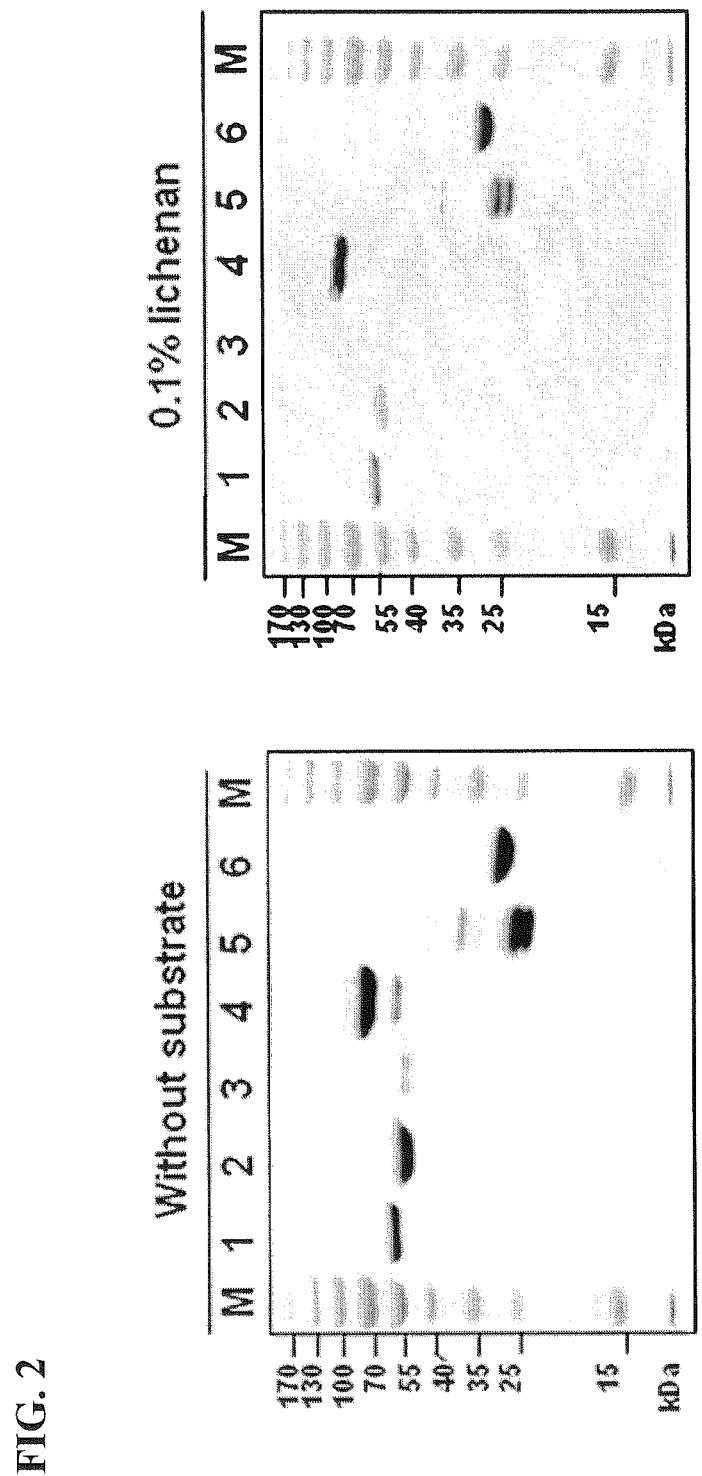
FIG. 2 is a set of SDS-PAGE gels showing the electrophoretic mobility of $TFs_{W203F}$ (having residues 1-248 of SEQ ID NO:3) and the hybrid glucanases on 12% SDS-PAGE gel without the addition of any substrate (left panel) and with 0.1% lichenan (right panel).

The N-terminal CBM domain $TmB_1$, catalytic domain $TmLam_{CD}$, and C-terminal CBM domain $TmB_2$ of TmLam (see SEQ ID NO:1) were amplified using PCR, and then ligated to the $TFs_{W203F}$ enzyme in different combinations. See FIG. 1. The confirmed gene sequences were subcloned into the pET26b(+) vector, and four recombinant chimera proteins, $TmB_1$-$TFs_{W203F}$ (50.3 kDa; having the sequence of SEQ ID NO:13 with or without the optional C-terminal taq), $TFs_{W203F}$-$TmB_2$ (46.3 kDa; having the sequence of SEQ ID NO:7 with or without the optional C-terminal taq), $TmB_1$-$TFs_{W203F}$-$TmB_2$ (66.8 kDa; having the sequence of SEQ ID NO:11 with or without the optional C-terminal taq) and $TFs_{W203F}$-$TmLam_{CD}$ (61.3 kDa; having the sequence of SEQ ID NO:9 with or without the optional C-terminal taq), were then successfully expressed in E. coli BL21(DE3) host cells as extracellular proteins. The recombinant proteins were purified from the culture media using a nickel affinity column, and protein purity was judged by SDS-PAGE (See FIG. 2) and zymography analyses (data not shown).

(2) Affinity SDS-PAGE Analysis of Substrate-Enzyme Binding

Figure 3:
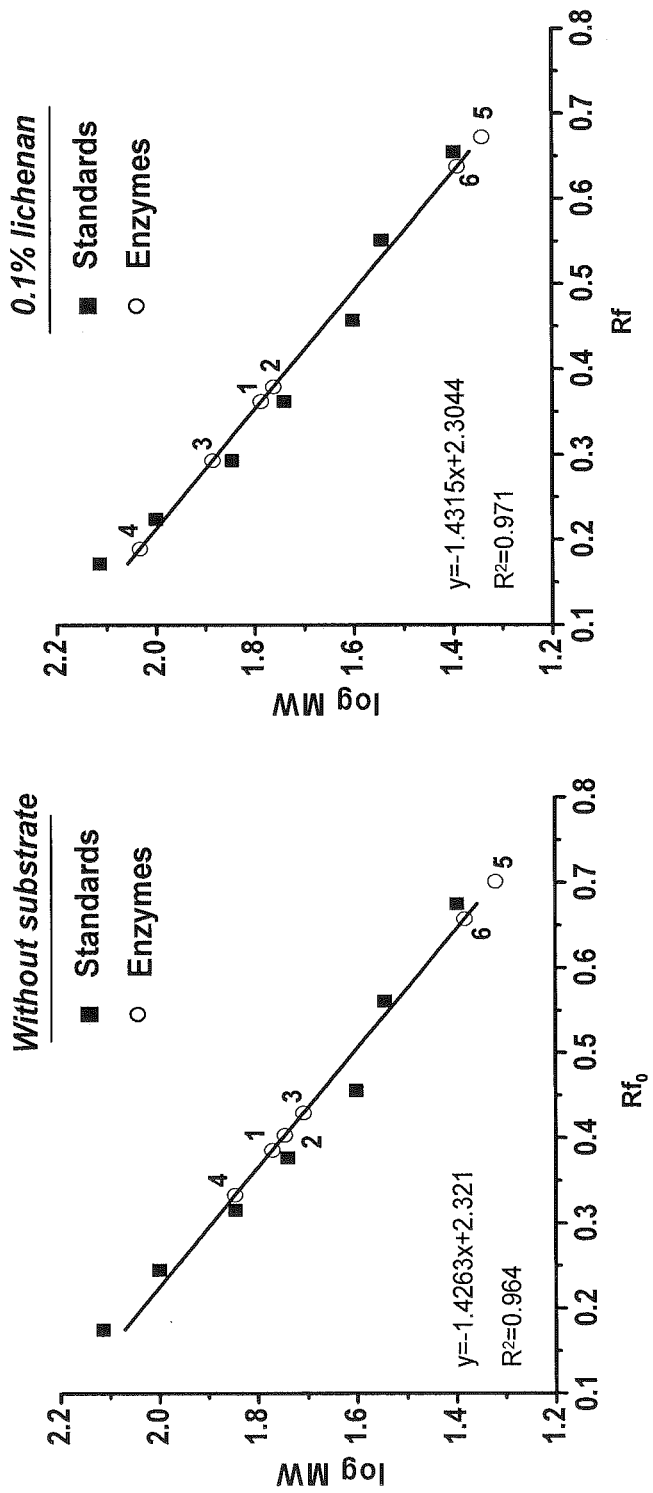
FIG. 3 is a set of graphs showing log MW vs. relative migration distance $Rf_0$ (without substrate; left panel) and Rf (with substrate; right panel) of protein standards and test enzymes. Protein standards (M); 1: $TFs_{W203F}$-$TmLam_{CD}$ (e.g., SEQ ID NO:9); 2: $TFs_{W203F}$-$TmB_2$ (e.g., SEQ ID NO:7); 3: $TmB_1$-$TFs_{W203}$ (e.g., SEQ ID NO:13); 4: $TmB_1$-$TFs_{W203F}$-$TmB_2$ (e.g., SEQ ID NO:11); 5: $TmLam_{CD}$ (e.g., residues 211-488 of SEQ ID NO:1); and 6: $TFs_{W203F}$ (having residues 1-248 of SEQ ID NO:3).

The substrate binding ability and behavior of the non-catalytic modules $TmB_1$ (having residues 19-176 of SEQ ID NO:1) and $TmB_2$ (having residues 495-642 of SEQ ID NO:1) from heterogeneous enzyme (TmLam) in the constructs of hybrid lichenases were evaluated by visualizing the relative mobility retardation of individual proteins in 12% SDS gel with or without the presence of 0.1% lichenan, along with a set of MW standards on the same gel. The relative mobility distances (Rf values) of the MW standards were used as the negative control of substrate retardation effect and as the reference for demonstrating the electrophoretic quality of the same set of protein samples separated in two independent gels with or without substrate. See FIG. 3. After electrophoresis, the proteins with a single or double catalytic domains, $TFs_{W203F}$ (having residues 1-248 of SEQ ID NO:3), $TmLam_{CD}$ (having residues 211-488 of SEQ ID NO:1) and $TFs_{W203F}$-$TmLam_{CD}$ (having the sequence of SEQ ID NO:9 with or without the optional C-terminal taq), only had little differences on their $Rf_0$ and Rf values obtained from plain gel and substrate-containing gel electrophoresis, respectively. See Table 2. The calculated retardation coefficient $K_r$ (>10) revealed no observable retardation (Zverlov, et al., 2001, Microbiology, 147, 621-629).

TABLE 2

Parental and hybrid proteins binding affinity to lichenan in 12% SDS-PAGE.

| Enzyme | Without substrate $Rf_0{}^a$ | 0.1% Lichenan $Rf^a$ | $K_r{}^b$ |
|---|---|---|---|
| $TFs_{W203F}$-$TmLam_{CD}$ | 0.39 | 0.36 | >10 |
| $TFs_{W203F}$-$TmB_2$ | 0.40 | 0.38 | >10 |
| $TmB_1$-$TFs_{W203F}$ | 0.43 | 0.29 | 2 |
| $TmB_1$-$TFs_{W203F}$-$TmB_2$ | 0.33 | 0.19 | 1 |
| $TmLam_{CD}$ | 0.70 | 0.67 | >10 |
| $TFs_{W203F}$ | 0.66 | 0.64 | >10 |

$^a$$Rf_0$ and Rf were defined as the ratio of the migration distance moved by each protein sample to the migration distance of the dye front in gel without and with substrate, respectively.
$^b$According to the Zverlov et al. method (2001), the retardation factor $K_r$ was calculated using the relative migration distance $Rf_0$ (without substrate) and Rf (with substrate): $K_r$ = Rf × $(Rf_0 - Rf)^{-1}$. No retardation ($K_r$ > 10); observable retardation ($K_r$ 6.0 – 0.1); strong retardation ($K_r$ < 0.1).

Notably, both $TmB_1$-$TFs_{W203F}$-$TmB_2$ (having the sequence of SEQ ID NO:11 with or without the optional C-terminal taq) and $TmB_1$-$TFs_{W203F}$ (having the sequence of SEQ ID NO:13 with or without the optional C-terminal taq) enzymes showed significant discrepancies between $Rf_0$ and Rf values, and as a result, $K_r$ values (1 and 2) were within the range representing retardation (6.0-0.1). Although little changes of both $Rf_0$ and Rf values and high $K_r$ value (>10) were observed for $TFs_{W203F}$-$TmB_2$ protein (having the sequence of SEQ ID NO:7 with or without the optional C-terminal taq), a group of smeared tailing bands distributed at higher MW range than the original protein band of $TFs_{W203}$-$TmB_2$ (having the sequence of SEQ ID NO:7 with or without the optional C-terminal taq) in lichenan-containing gel, suggesting retardation occurred. These results indicate that CBMs from thermophilic *T. maritima* could function normally for substrate binding when fused with $TFs_{W203F}$ (having residues 1-248 of SEQ ID NO:3) from mesophilic *F. succinogenes*.

(3) Kinetic Properties of Parental and Hybrid Glucanases

The kinetic properties of purified parental $TFs_{W203F}$ (having residues 1-248 of SEQ ID NO:3), $TmLam_{CD}$ (having residues 211-488 of SEQ ID NO:1) and their hybrid glucanases were determined under their respective optimal pH and temperature, with lichenan and/or laminarin as the substrate. The values for the Michaelis constant ($K_M$), turnover number ($k_{cat}$), and catalytic efficiency ($k_{cat}/K_M$) are presented in Table 3.

To compare the specific activities among the enzymes with differing molecular mass in this study, the specific activity is expressed as unit per nmol (U/nmol) of the protein. When lichenan was used as the substrate, the specific activity, $k_{cat}$, $K_M$ and $k_{cat}/K_M$ of $TFs_{W203F}$ (having residues 1-248 of SEQ ID NO:3) were determined as 626±38 U/nmol, 10100 s$^{-1}$, and 5.3±0.6 mg/ml, and 1908 s$^{-1}$ (mg/ml)$^{-1}$, respectively. Comparing the kinetic data of the truncated mutant $TFs_{W203F}$ (having residues 1-248 of SEQ ID NO:3) with the truncated wild-type PCR-TF-glucanase from the same organism *Fibrobacter succinogenes* (Wen et al., 2005, Biochemistry, 44, 9197-9205), $TFs_{W203F}$ (having residues 1-248 of SEQ ID NO:3) showed a 1.4-fold increase in catalytic efficiency [1908 vs. 1358 s$^{-1}$ (mg/ml)$^{-1}$]. $TFs_{W203F}$ (having residues 1-248 of SEQ ID NO:3) was thus used as the parental enzyme to create various hybrid enzymes in this study.

The kinetic data in Table 3 show that the hybrid enzymes, $TmB_1$-$TFs_{W203F}$ (having the sequence of SEQ ID NO:13 with or without the optional C-terminal taq), $TFs_{W203F}$-$TmB_2$ (having the sequence of SEQ ID NO:7 with or without the optional C-terminal taq) and $TmB_1$-$TFs_{W203F}$-$TmB_2$ (having the sequence of SEQ ID NO:11 with or without the optional C-terminal taq), each had either a slight increased or very similar specific activity and turnover number (~1.1-fold) as compared to that of $TFs_{W203F}$ (having residues 1-248 of SEQ ID NO:3), while a slight decrease (1.2-fold) was found in $TFs_{W203F}$-$TmLam_{CD}$ (having the sequence of SEQ ID NO:9 with or without the optional C-terminal taq). The $K_M$ for lichenan increased 2.0-fold in $TmB_1$-$TFs_{W203F}$ (having the sequence of SEQ ID NO:13 with or without the optional C-terminal taq) and 2.6-fold in $TFs_{W203F}$-$TmLam_{CD}$ (having the sequence of SEQ ID NO:9 with or without the optional C-terminal taq), and decreased slightly (1.3-fold) in $TmB_1$-$TFs_{W203F}$-$TmB_2$ (having the sequence of SEQ ID NO:11 with or without the optional C-terminal taq). Given this, the catalytic efficiency of the hybrid enzymes increased by 1.5-fold in $TmB_1$-$TFs_{W203F}$-$TmB_2$ (having the sequence of SEQ ID NO:11 with or without the optional C-terminal taq), but decreased, by 1.8-fold and 3.1-fold respectively, in $TmB_1$-$TFs_{W203F}$ (having the sequence of SEQ ID NO:13 with or without the optional C-terminal taq) and $TFs_{W203F}$-$TmLam_{CD}$ (having the sequence of SEQ ID NO:9 with or without the optional C-terminal taq) relative to that of $TFs_{W203F}$ (having residues 1-248 of SEQ ID NO:3) (see Table 3). Notably, $TmLam_{CD}$ (having residues 211-488 of SEQ ID NO:1) also revealed activity and affinity toward lichenan, with the specific activity, $k_{cat}$, $K_M$ and $k_{cat}/K_M$ determined as 2.3±0.1 U/nmol, 38 s$^{-1}$, 8.3±0.9 mg/ml and 5 s$^{-1}$ (mg/ml)$^{-1}$, respectively.

TABLE 3

Kinetic properties of parental $TFs_{W203F}$ and hybrid glucanases

| Enzyme | Specific Activity[g] U/nmol | $k_{cat}$ s$^{-1}$ | $K_M$ mg/ml | $k_{cat}/K_M$ s$^{-1}$ (mg/ml)$^{-1}$ | Opt. Reaction Conditions[e] °C./pH |
|---|---|---|---|---|---|
| PCR-TF-glucanase[a,b] | 233 ± 10 | 3911 | 2.9 ± 0.1 | 1358 | 50/6.0 |
| $TFs_{W203F}$[a] | 626 ± 38 | 10100 | 5.3 ± 0.6 | 1908 | 45/6.0 |
| $TFs_{W203F}$[c] | N.D.[f] | N.D.[f] | N.D.[f] | N.D.[f] | 45/7.0 |
| $TmB_1$-$TFs_{W203F}$[a,d] | 690 ± 8 | 11500 | 10.7 ± 0.2 | 1075 | 45/6.0 |
| $TFs_{W203F}$-$TmB_2$[a,d] | 658 ± 2 | 10960 | 5.5 ± 0.0 | 1997 | 45/6.0 |
| $TmB_1$-$TFs_{W203F}$-$TmB_2$[a,d] | 685 ± 1 | 11420 | 4.0 ± 0.0 | 2834 | 45/6.0 |
| $TFs_{W203F}$-$TmLam_{CD}$[a] | 514 ± 1 | 8570 | 14.0 ± 0.1 | 611 | 45/6.0 |
| $TFs_{W203F}$-$TmLam_{CD}$[c] | 23.3 ± 0.0 | 389 | 5.0 ± 0.0 | 78 | 95/8.0 |
| $TmLam_{CD}$[a] | 2.3 ± 0.1 | 38 | 8.3 ± 0.9 | 5 | 95/6.0 |
| $TmLam_{CD}$[c] | 6.5 ± 0.3 | 109 | 1.3 ± 0.2 | 82 | 95/6.0 |

[a]The kinetic study was performed with lichenan used as a substrate.
[b]Data from Wen et al. 2005.
[c]The kinetic study was performed with laminarin used as a substrate.
[d]The kinetic study performed with laminarin used as a substrate showed no detectable activity.
[e]The enzymatic reaction was performed at the respective optimal temperatures and pHs as indicated.
[f]N.D.: Activity not detected.
[g]One unit of enzyme activity was defined as the amount of enzyme required to produce 1 μmol of reducing sugar per minute.

When laminarin was used as the substrate in the activity assays, $TFs_{W203F}$ (having residues 1-248 of SEQ ID NO:3) showed no activity, even with a protein concentration four hundred times higher than that where lichenan was used as the substrate. The specific activity, $k_{cat}$, $K_M$ and $k_{cat}/K_M$ of $TmLam_{CD}$ (having residues 211-488 of SEQ ID NO:1) were 6.5±0.3 U/nmol, 109 s$^{-1}$, 1.3±0.2 mg/ml, and 82 s$^{-1}$ (mg/ml)$^{-1}$ respectively. Although the $TFs_{W203F}$ (having residues 1-248 of SEQ ID NO:3) enzyme did not show any activity in the presence of laminarin, when it was fused to $TmLam_{CD}$ (having residues 211-488 of SEQ ID NO:1) to form the hybrid $TFs_{W203F}$-$TmLam_{CD}$ (having the sequence of SEQ ID NO:9 with or without the optional C-terminal taq) enzyme, it displayed superior specific activity and $k_{cat}$ (3.6-fold increase) to $TmLam_{CD}$ (having residues 211-488 of SEQ ID NO:1), with a value of 23.3±0.0 U/nmol and 389 s$^{-1}$, though the $k_{cat}/K_M$ of the hybrid enzyme remained similar to that of $TmLam_{CD}$ (having residues 211-488 of SEQ ID NO:1) [78 vs. 82 s$^{-1}$ (mg/ml)$^{-1}$], owing to an increase in $K_M$ value (5.0±0.0 mg/ml). See Table 3.

(4) Temperature and pH Effects on Parental and Hybrid Glucanases

The effects of temperature and pH on the enzymatic activity of the purified parental and hybrid glucanases were also examined. The optimal temperature for $TFs_{W203F}$ (having residues 1-248 of SEQ ID NO:3), $TFs_{W203F}$-$TmLam_{CD}$ (having the sequence of SEQ ID NO:9 with or without the optional C-terminal taq), $TmB_1$-$TFs_{W203F}$ (having the sequence of SEQ ID NO:13 with or without the optional C-terminal taq), $TFs_{W203F}$-$TmB_2$ (having the sequence of SEQ ID NO:7 with or without the optional C-terminal taq) and $TmB_1$-$TFs_{W203F}$-$TmB_2$ (having the sequence of SEQ ID NO:11 with or without the optional C-terminal taq) was between 45° C. and 50° C., and an optimal pH of 6.0 or 7.0 was observed. The optimal temperature of $TmLam_{CD}$ (having residues 211-488 of SEQ ID NO:1) was approximately 95° C. All of the enzymes exhibited similar pH response profiles in terms of their activities when the individual enzymes were pre-incubated at room temperature for one hour in buffers with pH values ranging from pH 3.0 to 9.0. All of the enzymes showed <20% residual activity after pH 3.0 pre-treatment, and little or no difference (85-100% activity) was found in the tested enzymes pre-incubated at pH 4.0-9.0 (data not shown).

Figure 4:
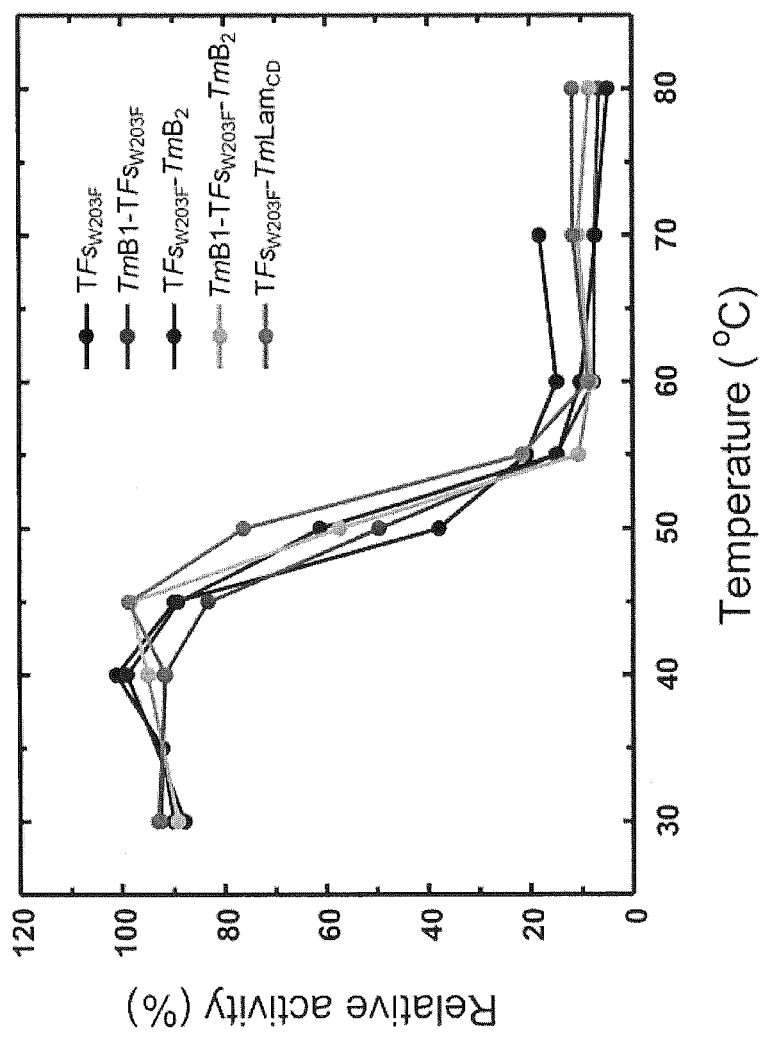
FIG. 4 is a graph showing the effect of temperature on the enzymatic activity of $TFs_{W203F}$ (having residues 1-248 of SEQ ID NO:3) and the hybrid glucanases. Purified enzymes were incubated for ten minutes at 30, 40, 45, 50, 55, 60, 70 and 80° C. in sodium phosphate buffer (50 mM, pH 7.0). Each assay was performed either in triplicate or in quadruplicate.

To investigate the influence of the newly-introduced protein domain(s) on the thermal stability of TFs$_{W203F}$ (having residues 1-248 of SEQ ID NO:3), the proteins were incubated individually for ten minutes at temperatures between the range of 30° C. and 80° C. in 5° C. steps, and the residual enzyme activities measured using lichenan as the substrate. As shown in FIG. 4, little difference in temperature sensitivity was observed at 30-45° C. in all test enzymes. When the temperature was increased to 50° C., TFs$_{W203F}$ (having residues 1-248 of SEQ ID NO:3) only retained 38% of its activity, whereas the TFs$_{W203F}$ (having residues 1-248 of SEQ ID NO:3) fused with TmLam$_{CD}$ (having residues 211-488 of SEQ ID NO:1) enzyme remained 76% active. Other hybrid enzymes were shown to retain between 50% and 62% of their original activity under the same treatment. In pre-treatment at ≥55° C., on the other hand, the enzymatic activity of all the tested enzymes fell significantly, to below 20%.

(5) CD and Fluorescence Spectrometric Analyses

Figure 5:
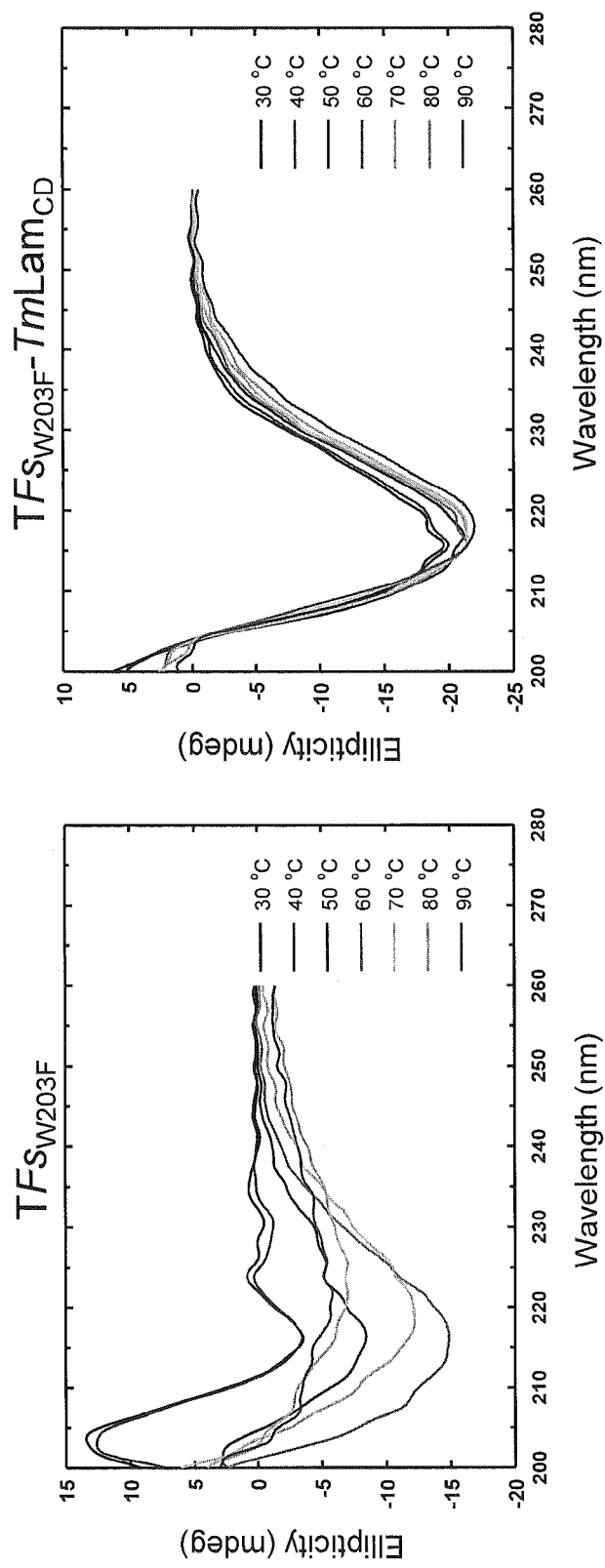
FIG. 5 is a set of graphs showing circular dichroism (CD) spectra of $TFs_{W203F}$ (having residues 1-248 of SEQ ID NO:3) (left panel) and $TFs_{W203F}$-$TmLam_{CD}$ (e.g., SEQ ID NO:9) (right panel) under heat treatment at the temperatures indicated.

Because TFs$_{W203F}$ (having residues 1-248 of SEQ ID NO:3) and TFs$_{W203F}$-TmLam$_{CD}$ (having the sequence of SEQ ID NO:9 with or without the optional C-terminal taq) exhibited the most differing temperature sensitivity at 50° C. out of the enzymes compared, we therefore examined their secondary structures at temperatures between 30° C. and 90° C. at 10° C. intervals, using CD spectroscopy. The CD spectral profile of TFs$_{W203F}$ protein (having residues 1-248 of SEQ ID NO:3) revealed no difference at 30° C. and 40° C., but protein unfolding and a substantial loss of structural integrity appeared when temperatures were elevated to 50° C. or 70° C., and protein denaturated at temperatures between 80° C. and 90° C., with random coiled spectra occurring. See FIG. 5. Surprisingly, only minor alterations were observed in the CD spectra of TFs$_{W203F}$-TmLam$_{CD}$ (having the sequence of SEQ ID NO:9 with or without the optional C-terminal taq) when the temperatures were increased from 30° C. to 90° C., which suggests that TFs$_{W203F}$-TmLam$_{CD}$ (having the sequence of SEQ ID NO:9 with or without the optional C-terminal taq) possesses superior thermal stability to TFs$_{W203F}$ (having residues 1-248 of SEQ ID NO:3)

Furthermore, fluorescence spectrometry was employed to investigate the structural integrity of TFs$_{W203F}$ (having residues 1-248 of SEQ ID NO:3) and TFs$_{W203F}$-TmLam$_{CD}$ (having the sequence of SEQ ID NO:9 with or without the optional C-terminal taq) glucanases under native (25° C.), heat-treated (50° C. and 75° C.), 8 M urea-denatured, and denatured/renatured conditions. At 25° C. and 50° C., the emission spectra of both glucanases showed similar profiles, with a maximum emission peak of 336 nm. See FIG. 6. When emission spectra were monitored at 75° C., however, the profile of TFs$_{W203F}$ (having residues 1-248 of SEQ ID NO:3) exhibited a significant bathochromic (red) shift, peaking at 344 nm, whereas the TFs$_{W203F}$-TmB$_2$ protein (having the sequence of SEQ ID NO:7 with or without the optional C-terminal taq) displayed little or no difference between 25° C., 50° C. and 75° C. When the enzymes were treated with denaturant 8 M urea, significant red shifts, with a maximum peak at 352 nm and a slight shoulder at 382 nm, were observed. The urea-denatured enzymes were then dialyzed against sodium phosphate buffer (50 mM, pH 7.0) for 24 hours in order to remove the denaturant and allow the protein to refold. The renatured enzymes were then analyzed for their fluorescence emission spectra under the same conditions.

Figure 6:
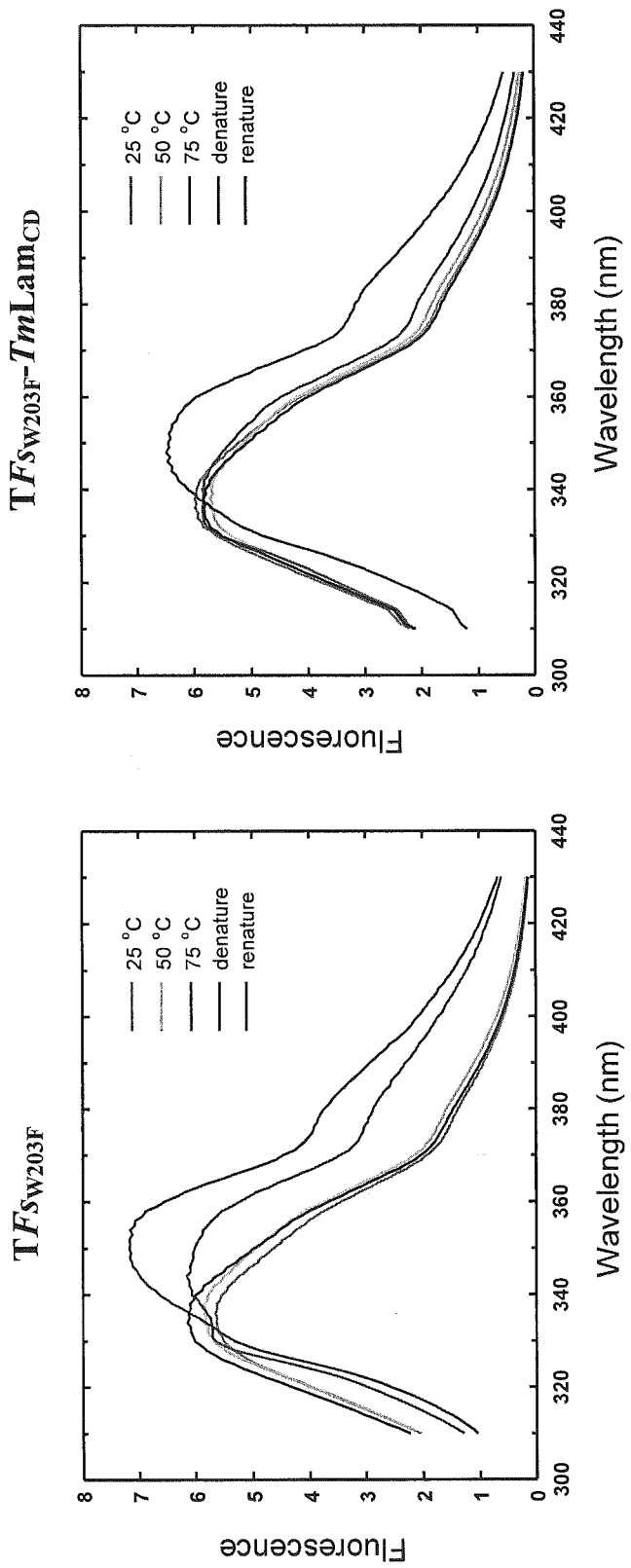
FIG. 6 is a set of graphs showing fluorescence emission spectra at 310-340 nm for $TFs_{W203F}$ (having residues 1-248 of SEQ ID NO:3) (left panel) and $TFs_{W203F}$-$TmLam_{CD}$ (e.g., SEQ ID NO:9) (right panel). Each enzyme comprised 30 µg/mL in sodium phosphate buffer (50 mM, pH 7.0) or in an 8 M urea-phosphate buffer (denatured). The excitation wavelength was 295 nm.

As shown in FIG. 6, the maximum spectra of both denatured and renatured proteins were shifted back to 336 nm and superimposed on the native protein spectrum, with few or no differences visible. These results indicate that, although the structure of TFs$_{W203F}$ (having residues 1-248 of SEQ ID NO:3) displays greater sensitivity to high temperatures than the hybrid TFs$_{W203F}$-TmLam$_{CD}$ (having the sequence of SEQ ID NO:9 with or without the optional C-terminal taq), it was possible to effectively refold both enzyme structures to a native-like structure after urea denaturing.

Figure 7:
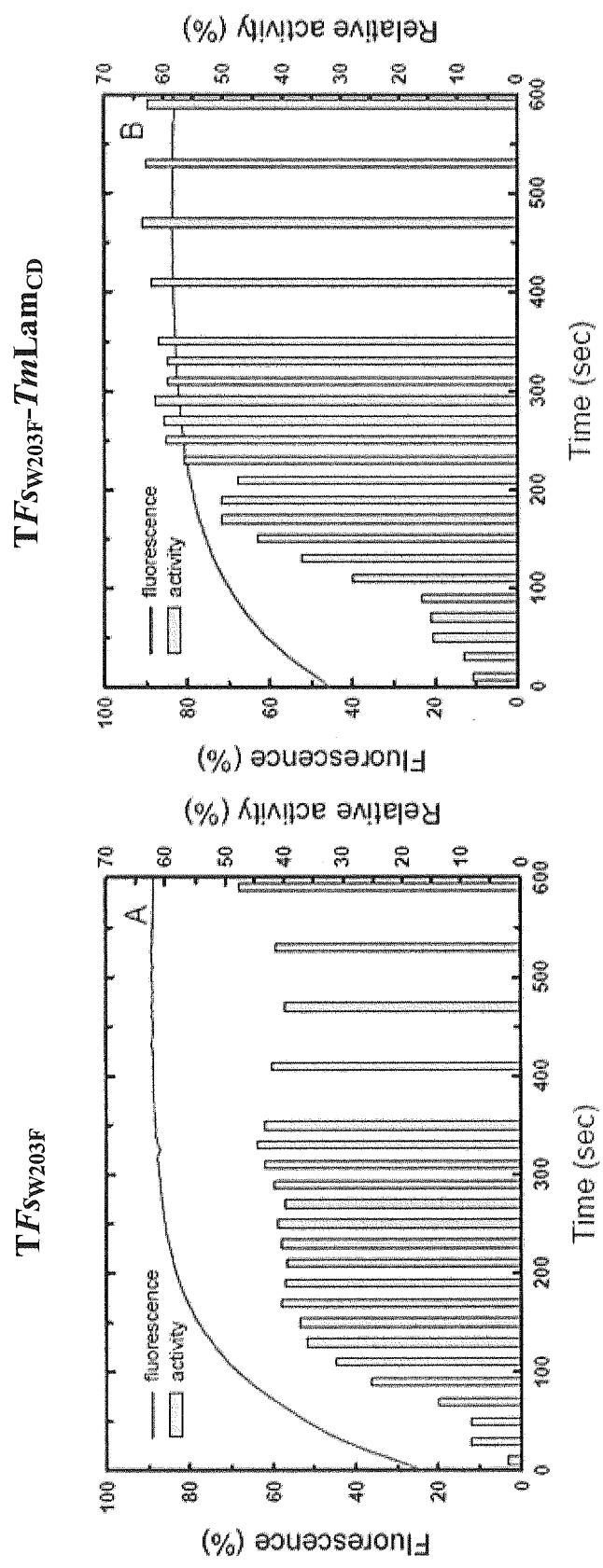
FIG. 7 is a set of graphs showing recovery of enzymatic activity and fluorescence emission intensity of $TFs_{W203F}$ (having residues 1-248 of SEQ ID NO:3) (left panel) and $TFs_{W203F}$-$TmLam_{CD}$ (e.g., SEQ ID NO:9) (right panel) at ambient temperature after heat treatment at 90° C. for ten minutes. The residual enzyme activity of heat-treated protein was measured every 18 seconds from when it was transferred from the incubator at 90° C. to ambient temperature (25° C.), in a ten-minute period. The fluorescence emission spectra of the treated enzymes were taken immediately after treatment at 90° C. and monitored for ten minutes.

(6) Protein Reactivation Profile of TFs$_{W203F}$ and TFs$_{W203F}$-TmLam$_{CD}$ To evaluate the recovery efficiency of enzymatic activity after high-temperature treatment (90° C., ten minutes), the activities of TFs$_{W203F}$ (having residues 1-248 of SEQ ID NO:3) and hybrid TFs$_{W203F}$-TmLam$_{CD}$ (having the sequence of SEQ ID NO:9 with or without the optional C-terminal taq) recovered at room temperature at different time intervals were examined, in parallel to monitoring the fluorescence emission spectra of the enzymes. As is shown in FIG. 7, within 110 seconds both TFs$_{W203F}$ (having residues 1-248 of SEQ ID NO:3) and hybrid TFs$_{W203F}$-TmLam$_{CD}$ (having the sequence of SEQ ID NO:9 with or without the optional C-terminal taq) recovered approximately 27-34% activity, and after a ten-minute recovery time, parental TFs$_{W203F}$ (having residues 1-248 of SEQ ID NO:3) and hybrid TFs$_{W203F}$-TmLam$_{CD}$ (having the sequence of SEQ ID NO:9 with or without the optional C-terminal taq) reached 48% and 63% of their original activities respectively. Meanwhile, the relative fluorescence intensity recovered 88% and 83% in TFs$_{W203F}$ (having residues 1-248 of SEQ ID NO:3) and TFs$_{W203F}$-TmLam$_{CD}$ (having the sequence of SEQ ID NO:9 with or without the optional C-terminal taq) respectively. Thermal stability is an important criterion for enzymes, especially as regards their applications in the brewing and animal feeds industry, where malting or feed pelleting processes usually operate at high temperatures (>90° C.) (Hong et al., 2009, J. Microbiol. Biotechnol., 19, 818-822). Hybrid TFs$_{W203F}$ capable of enduring extreme conditions and gradually recovering its enzymatic activity at room temperature may therefore be desirable from an industrial point of view.

(7) Structural Modeling

By modeling, β-1,3-1,4-celloheptaose (representing the original substrate lichenan) fitted neatly into the catalytic cleft of TFs$_{W203F}$ (having residues 1-248 of SEQ ID NO:3), but laminarihexose (representative of laminarin) did not fit well, and indeed collided with the residues at the active site. The three sequential β-1,3-glucose moieties in the modeled laminarihexose did, however, fit neatly into the active site of TFs$_{W203F}$ (having residues 1-248 of SEQ ID NO:3). Because the TFs$_{W203F}$-TmLam$_{CD}$ (having the sequence of SEQ ID NO:9 with or without the optional C-terminal taq) showed an improvement (a 3.6-fold increase) in specific activity against laminarin as compared to TmLam$_{CD}$ (having residues 211-488 of SEQ ID NO:1) alone, and because we have recently demonstrated that laminaritriose is the major product of TmLam$_{CD}$ (having residues 211-488 of SEQ ID NO:1) toward the substrate laminarin (Jeng et al., 2011, J.

Biol. Chem., 286, 45030-45040), the TFs$_{W203F}$ domain in TFs$_{W203F}$-TmLam$_{CD}$ (having the sequence of SEQ ID NO:9 with or without the optional C-terminal taq) may play a role in capturing the product laminaritriose, which results in the facilitation and enhancement of the catalytic activity of TFs$_{W203F}$-TmLam$_{CD}$ (having the sequence of SEQ ID NO:9 with or without the optional C-terminal taq) toward laminarin. However, a slight decrease (2.6~3.7-fold) in binding affinity with lichenan and laminarin was also observed in the hybrid enzyme as compared with the TFs$_{W203F}$ (having residues 1-248 of SEQ ID NO:3) and TmLam$_{CD}$ domain (having residues 211-488 of SEQ ID NO:1) alone. This suggest that there might be some subtle steric hindrance from other domains in the hybrid glucanases. On the other hand, in the modeled structures of TmLam$_{CD}$ (having residues 211-488 of SEQ ID NO:1) complexed with β-1,3-1,4-celloheptaose and laminarihexose, the oligosaccharides all fitted nicely into the catalytic cleft of the laminarinase, which in combination with the kinetic data indicated that TmLam$_{CD}$ (having residues 211-488 of SEQ ID NO:1) is capable of hydrolyzing both types of β-glucan substrate.

On the basis of the structural modeling, both TmB$_1$ (having residues 19-176 of SEQ ID NO:1) and TmB$_2$ (having residues 495-642 of SEQ ID NO:1) formed a concave catalytic-like open cleft like that of TFs$_{W203F}$ (having residues 1-248 of SEQ ID NO:3), which may contribute to holding the lichenan chain in place, and in turn to facilitating the efficient hydrolysis of lichenan in TFs$_{W203F}$ (having residues 1-248 of SEQ ID NO:3). Furthermore, in comparison to the TmB$_1$ (having residues 19-176 of SEQ ID NO:1) and TmB$_2$ (having residues 495-642 of SEQ ID NO:1) structures modeled, the narrow gate formed by two tryptophans in the binding cleft of TmB$_2$ (having residues 495-642 of SEQ ID NO:1) (about 7.6-8.2 Å) is wider than the carbohydrate binding cleft of TmB$_1$ (having residues 19-176 of SEQ ID NO:1) (about 6.3-7.3 Å) for polysaccharide binding, which may explain why TmB$_1$-TFs$_{W203F}$ (having the sequence of SEQ ID NO:13 with or without the optional C-terminal taq) had a lower lichenan-binding affinity than TFs$_{W203F}$-TmB$_2$ (having the sequence of SEQ ID NO:7 with or without the optional C-terminal taq). The co-existence of both CBMs in TFs$_{W203F}$ (having residues 1-248 of SEQ ID NO:3) do, however, compensate somewhat for the weaker substrate binding, with a consequent slight decrease in K$_M$ value, and a corresponding improvement in the overall catalytic efficiency of TmB$_1$-TFs$_{W203F}$-TmB$_2$ (having the sequence of SEQ ID NO:11 with or without the optional C-terminal taq) as compared to the single domain enzyme TFs$_{W203F}$ (having residues 1-248 of SEQ ID NO:3) [2834 vs. 1908 s$^{-1}$ (mg/ml)$^{-1}$].

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A fusion polypeptide comprising:
   (a) a first segment containing a TFs$_{W203F}$ polypeptide having residues 1-248 of SEQ ID NO:3; and
   (b) a second segment containing a catalytic domain of TmLam having a sequence that is at least 90% identical to residues 211-488 of SEQ ID NO:1;
   wherein the fusion polypeptide has a glucanase activity and an amino acid sequence that is at least 90% identical to the amino acid sequence of SEQ ID NO:5 or 9.

2. The fusion polypeptide of claim 1, wherein the polypeptide has an amino acid sequence that is at least 95% identical to the amino acid sequence of SEQ ID NO:5 or 9.

3. The fusion polypeptide of claim 1, wherein the polypeptide has the amino acid sequence of SEQ ID NO:5 or 9.

4. The fusion polypeptide of claim 1, wherein the polypeptide has residues 1-532 of SEQ ID NO:9.

5. The fusion polypeptide of claim 1, wherein the polypeptide has residues 1-538 of SEQ ID NO:5.

* * * * *

SEQUENCE LISTING

```
<160> NUMBER OF SEQ ID NOS: 25

<210> SEQ ID NO 1
<211> LENGTH: 642
<212> TYPE: PRT
<213> ORGANISM: Thermotoga maritima

<400> SEQUENCE: 1

Met Met Ser Arg Leu Val Phe Ala Leu Leu Leu Phe Pro Val Phe Ile
1               5                   10                  15

Leu Ala Gln Asn Ile Leu Gly Asn Ala Ser Phe Asp Glu Pro Ile Leu
            20                  25                  30

Ile Ala Gly Val Asp Ile Asp Pro Pro Ala Glu Asp Gly Ser Ile Asp
        35                  40                  45

Thr Gly Gly Asn Trp Val Phe Phe Thr Asn Ser Asn Gly Glu Gly Thr
    50                  55                  60

Ala Arg Val Glu Asn Gly Val Leu Val Val Glu Ile Thr Asn Gly Gly
65                  70                  75                  80

Asp His Thr Trp Ser Val Gln Ile Ile Gln Ala Pro Ile Arg Val Glu
                85                  90                  95

Lys Leu His Lys Tyr Arg Val Ser Phe Arg Ala Lys Ala Ser Ser Gln
            100                 105                 110

Lys Asn Ile Gly Val Lys Ile Gly Gly Thr Ala Gly Arg Gly Trp Thr
        115                 120                 125

Ala Tyr Asn Pro Gly Thr Asp Glu Ser Gly Gly Met Val Phe Glu Leu
    130                 135                 140
```

-continued

```
Gly Thr Asp Trp Gln Lys Tyr Glu Phe Glu Phe Val Met Arg Gln Glu
145                 150                 155                 160

Thr Asp Glu Asn Ala Arg Phe Glu Phe Gln Leu Gly Arg Tyr Thr Gly
                165                 170                 175

Thr Val Trp Ile Asp Asp Val Val Met Glu Asp Ile Gly Val Leu Glu
            180                 185                 190

Val Ser Gly Glu Glu Asn Glu Ile Tyr Thr Glu Glu Asp Glu Asp Lys
        195                 200                 205

Val Glu Asp Trp Gln Leu Val Trp Ser Gln Glu Phe Asp Gly Val
    210                 215                 220

Ile Asp Pro Asn Ile Trp Asn Phe Glu Ile Gly Asn Gly His Ala Lys
225                 230                 235                 240

Gly Ile Pro Gly Trp Gly Asn Gly Glu Leu Glu Tyr Tyr Thr Asp Glu
                245                 250                 255

Asn Ala Phe Val Glu Asn Gly Cys Leu Val Ile Glu Ala Arg Lys Glu
                260                 265                 270

Gln Val Ser Asp Glu Tyr Gly Thr Tyr Asp Tyr Thr Ser Ala Arg Met
        275                 280                 285

Thr Thr Glu Gly Lys Phe Glu Ile Lys Tyr Gly Lys Ile Glu Ile Arg
290                 295                 300

Ala Lys Leu Pro Lys Gly Lys Gly Ile Trp Pro Ala Leu Trp Met Leu
305                 310                 315                 320

Gly Asn Asn Ile Gly Glu Val Gly Trp Pro Thr Cys Gly Glu Ile Asp
                325                 330                 335

Ile Met Glu Met Leu Gly His Asp Thr Arg Thr Val Tyr Gly Thr Ala
                340                 345                 350

His Gly Pro Gly Tyr Ser Gly Gly Ala Ser Ile Gly Val Ala Tyr His
                355                 360                 365

Leu Pro Glu Gly Val Pro Asp Phe Ser Glu Asp Phe His Ile Phe Ser
        370                 375                 380

Ile Glu Trp Asp Glu Asp Glu Val Glu Trp Tyr Val Asp Gly Gln Leu
385                 390                 395                 400

Tyr His Val Leu Ser Lys Asp Glu Leu Ala Glu Leu Gly Leu Glu Trp
                405                 410                 415

Val Phe Asp His Pro Phe Phe Leu Ile Leu Asn Val Ala Val Gly Gly
            420                 425                 430

Tyr Trp Pro Gly Tyr Pro Asp Glu Thr Thr Gln Phe Pro Gln Arg Met
        435                 440                 445

Tyr Ile Asp Tyr Ile Arg Val Tyr Lys Asp Met Asn Pro Glu Thr Ile
450                 455                 460

Thr Gly Glu Val Asp Asp Cys Glu Tyr Glu Gln Ala Gln Gln Ala
465                 470                 475                 480

Gly Pro Glu Val Thr Tyr Glu Gln Ile Asn Asn Gly Thr Phe Asp Glu
                485                 490                 495

Pro Ile Val Asn Asp Gln Ala Asn Asn Pro Asp Glu Trp Phe Ile Trp
            500                 505                 510

Gln Ala Gly Asp Tyr Gly Ile Ser Gly Ala Arg Val Ser Asp Tyr Gly
        515                 520                 525

Val Arg Asp Gly Tyr Ala Tyr Ile Thr Ile Ala Asp Pro Gly Thr Asp
    530                 535                 540

Thr Trp His Ile Gln Phe Asn Gln Trp Ile Gly Leu Tyr Arg Gly Lys
545                 550                 555                 560

Thr Tyr Thr Ile Ser Phe Lys Ala Lys Ala Asp Thr Pro Arg Pro Ile
```

```
                565                 570                 575
Asn Val Lys Ile Leu Gln Asn His Asp Pro Trp Thr Asn Tyr Phe Ala
            580                 585                 590

Gln Thr Val Asn Leu Thr Ala Asp Trp Gln Thr Phe Thr Phe Thr Tyr
        595                 600                 605

Thr His Pro Asp Asp Ala Asp Glu Val Val Gln Ile Ser Phe Glu Leu
    610                 615                 620

Gly Glu Gly Thr Ala Thr Thr Ile Tyr Phe Asp Asp Val Thr Val Ser
625                 630                 635                 640

Pro Gln

<210> SEQ ID NO 2
<211> LENGTH: 1921
<212> TYPE: DNA
<213> ORGANISM: Artificial sequence
<220> FEATURE:
<223> OTHER INFORMATION: Synthetic polynucleotide

<400> SEQUENCE: 2
gatggccatg gctcaaaaca tccttggcaa cgcttctttc gatgaaccaa ttctcatcgc      60
aggtgtggat atagacccac ccgcagagga tggctctata gacacaggag gaaactgggt     120
attcttcacc aattcaaacg gtgagggaac ggctcgagtc gaaaacggcg ttctcgtggt     180
tgagataaca aacggaggag atcacacctg gtcggttcag atcatacagg ctcccatacg     240
tgttgagaaa ctccacaagt acagagtttc tttccgagcc aaggcttcct ctcaaaagaa     300
catcggggtg aagataggag gaacggccgg aagaggatgg accgcgtaca accccggtac     360
cgacgaatcc ggcggcatgg tcttcgagct cggaacagat tggcagaagt acgagttcga     420
attcgtcatg agacaggaga ccgatgaaaa tgctcgtttc gagtttcagc ttggaaggta     480
taccggcacg gtctggatag acgacgtagt gatggaggac atcggtgttc tcgaggtaag     540
cggtgaggaa aacgaaatct acaccgagga ggatgaagac aaagtggaag actggcagct     600
cgtttggagt caggagttcg atgacggtgt tatcgatccg aacatctgga acttcgagat     660
aggaaacggt catgcaaaag gtattccagg ctggggtaac ggggaactcg agtactatac     720
agacgaaaac gcgttcgttg agaacggctg tcttgtgatt gaggcaagaa agaacaggt     780 ttccgatgag tacggaacct acgactacac ctcagccagg atgaccacag aaggaaaatt     840
cgaaataaag tacggaaaaa tcgaaataag ggcaaaactt ccaaaaggaa aaggtatctg     900
gcccgctctc tggatgctcg aaacaacat aggagaggtc ggatggccca cctgtggtga     960
gatagacatc atggaaatgc ttggccacga caccagaacc gtttatggaa cagcacacgg    1020
tccgggatat tctggtggtg cgagtatagg tgttgcctat catcttccag aaggagttcc    1080
tgatttctcc gaagacttcc acattttctc catcgagtgg gacgaagacg aagtggagtg    1140
gtacgtggac ggacagctct accacgtcct cagcaaggat gaactggccg aactcggtct    1200
tgagtgggtt ttcgaccatc cgttcttcct cattctgaac gttgccgtgg aggctactg    1260 gccgggttat cccgacgaaa ccacccaatt cccgcagaga atgtacatcg actacatcag    1320
agtctataaa gatatgaatc cggaaacaat caccggggaa gtggatgact gcgaatatga    1380
acaagcacag cagcaggcag gtcccgaggt gacctatgaa cagataaata acggcacttt    1440
cgacgaacct attgtgaacg atcaggccaa caacccggac gaatggttca tttggcaggc    1500
gggagattac gggatcagcg gtgccagggt ctccgattac ggtgtcaggg atggctacgc    1560
ttatatcacg atagccgatc ctggaactga cacgtggcat attcagttca accagtggat    1620
```

```
aggtctttac agaggaaaaa cctacaccat ttctttcaaa gcaaaagcgg atacaccaag   1680
acctataaat gtgaaaattc tgcagaatca cgatccctgg accaactatt ttgctcaaac   1740
ggtgaatctc acagcggact ggcagacgtt cacgttcacc tacacgcatc cagacgatgc   1800
ggatgaggtc gttcagatca gtttcgaact cggagaagga acggcaacta cgatttattt   1860
cgatgatgtc acggtgagcc ctcaagcggc cgcactcgag caccaccacc accaccactg   1920
a                                                                  1921
```

<210> SEQ ID NO 3
<211> LENGTH: 267
<212> TYPE: PRT
<213> ORGANISM: Artificial sequence
<220> FEATURE:
<223> OTHER INFORMATION: Synthetic polypeptide

<400> SEQUENCE: 3

Met Val Ser Ala Lys Asp Phe Ser Gly Ala Glu Leu Tyr Thr Leu Glu
1               5                   10                  15

Glu Val Gln Tyr Gly Lys Phe Glu Ala Arg Met Lys Met Ala Ala Ala
            20                  25                  30

Ser Gly Thr Val Ser Ser Met Phe Leu Tyr Gln Asn Gly Ser Glu Ile
        35                  40                  45

Ala Asp Gly Arg Pro Trp Val Glu Val Asp Ile Glu Val Leu Gly Lys
    50                  55                  60

Asn Pro Gly Ser Phe Gln Ser Asn Ile Ile Thr Gly Lys Ala Gly Ala
65                  70                  75                  80

Gln Lys Thr Ser Glu Lys His His Ala Val Ser Pro Ala Ala Asp Gln
                85                  90                  95

Ala Phe His Thr Tyr Gly Leu Glu Trp Thr Pro Asn Tyr Val Arg Trp
            100                 105                 110

Thr Val Asp Gly Gln Glu Val Arg Lys Thr Glu Gly Gly Gln Val Ser
        115                 120                 125

Asn Leu Thr Gly Thr Gln Gly Leu Arg Phe Asn Leu Trp Ser Ser Glu
    130                 135                 140

Ser Ala Ala Trp Val Gly Gln Phe Asp Glu Ser Lys Leu Pro Leu Phe
145                 150                 155                 160

Gln Phe Ile Asn Trp Val Lys Val Tyr Lys Tyr Thr Pro Gly Gln Gly
                165                 170                 175

Glu Gly Gly Ser Asp Phe Thr Leu Asp Trp Thr Asp Asn Phe Asp Thr
            180                 185                 190

Phe Asp Gly Ser Arg Trp Gly Lys Gly Asp Phe Thr Phe Asp Gly Asn
        195                 200                 205

Arg Val Asp Leu Thr Asp Lys Asn Ile Tyr Ser Arg Asp Gly Met Leu
    210                 215                 220

Ile Leu Ala Leu Thr Arg Lys Gly Gln Glu Ser Phe Asn Gly Gln Val
225                 230                 235                 240

Pro Arg Asp Asp Glu Pro Ala Pro Asn Ser Ser Val Asp Lys Leu
                245                 250                 255

Ala Ala Ala Leu Glu His His His His His His
            260                 265

<210> SEQ ID NO 4
<211> LENGTH: 804
<212> TYPE: DNA
<213> ORGANISM: Artificial sequence
<220> FEATURE:
<223> OTHER INFORMATION: Synthetic polynucleotide

<400> SEQUENCE: 4

| | | |
|---|---|---|
| atggttagcg caaaggattt tagcggtgcc gaactctaca cgttagaaga agttcagtac | 60 |
| ggtaagtttg aagcccgtat gaagatggca gccgcatcgg gaacagtcag ttccatgttc | 120 |
| ctctaccaga atggttccga aatcgccgat ggaaggccct gggtagaagt ggatattgaa | 180 |
| gttctcggca agaatccggg cagtttccag tccaacatca ttaccggtaa ggccggcgca | 240 |
| caaaagacta gcgaaaagca ccatgctgtt agccccgccg ccgatcaggc tttccacacc | 300 |
| tacggtctcg aatggactcc gaattacgtc cgctggactg ttgacggtca ggaagtccgc | 360 |
| aagacggaag gtggccaggt ttccaacttg acaggtacac agggactccg tttttaacctt | 420 |
| tggtcgtctg agagtgcggc ttgggttggc cagttcgatg aatcaaagct tccgcttttc | 480 |
| cagttcatca actgggtcaa ggtttataag tatacgccgg ccagggcga aggcggcagc | 540 |
| gactttacgc ttgactggac cgacaatttt gacacgtttg atggctcccg ctggggcaag | 600 |
| ggtgacttca catttgacgg taaccgtgtc gacctcaccg acaagaacat ctactccaga | 660 |
| gatggcatgt tgatcctcgc cctcacccgc aaaggtcagg aaagcttcaa cggccaggtt | 720 |
| ccgagagatg acgaacctgc tccgaattcg agctccgtcg acaagcttgc ggccgcactc | 780 |
| gagcaccacc accaccacca ctga | 804 |

<210> SEQ ID NO 5
<211> LENGTH: 557
<212> TYPE: PRT
<213> ORGANISM: Artificial sequence
<220> FEATURE:
<223> OTHER INFORMATION: Synthetic polypeptide

<400> SEQUENCE: 5

Met Glu Asp Glu Asp Lys Val Glu Asp Trp Gln Leu Val Trp Ser Gln
1               5                   10                  15

Glu Phe Asp Asp Gly Val Ile Asp Pro Asn Ile Trp Asn Phe Glu Ile
                20                  25                  30

Gly Asn Gly His Ala Lys Gly Ile Pro Gly Trp Gly Asn Gly Glu Leu
            35                  40                  45

Glu Tyr Tyr Thr Asp Glu Asn Ala Phe Val Glu Asn Gly Cys Leu Val
        50                  55                  60

Ile Glu Ala Arg Lys Glu Gln Val Ser Asp Glu Tyr Gly Thr Tyr Asp
65                  70                  75                  80

Tyr Thr Ser Ala Arg Met Thr Thr Glu Gly Lys Phe Glu Ile Lys Tyr
                85                  90                  95

Gly Lys Ile Glu Ile Arg Ala Lys Leu Pro Lys Gly Lys Gly Ile Trp
            100                 105                 110

Pro Ala Leu Trp Met Leu Gly Asn Asn Ile Gly Glu Val Gly Trp Pro
        115                 120                 125

Thr Cys Gly Glu Ile Asp Ile Met Glu Met Leu Gly His Asp Thr Arg
130                 135                 140

Thr Val Tyr Gly Thr Ala His Gly Pro Gly Tyr Ser Gly Gly Ala Ser
145                 150                 155                 160

Ile Gly Val Ala Tyr His Leu Pro Glu Gly Val Pro Asp Phe Ser Glu
                165                 170                 175

Asp Phe His Ile Phe Ser Ile Glu Trp Asp Gly Asp Glu Val Glu Trp
            180                 185                 190

Tyr Val Asp Gly Gln Leu Tyr His Val Leu Ser Lys Asp Glu Leu Ala
            195                 200                 205

Glu Leu Gly Leu Glu Trp Val Phe Asp His Pro Phe Leu Ile Leu
    210                 215                 220

Asn Val Ala Val Gly Gly Tyr Trp Pro Gly Tyr Pro Asp Glu Thr Thr
225                 230                 235                 240

Gln Phe Pro Gln Arg Met Tyr Ile Asp Tyr Ile Arg Val Tyr Lys Asp
                245                 250                 255

Met Asn Pro Glu Thr Ile Thr Gly Glu Val Asp Asp Cys Glu Tyr Glu
            260                 265                 270

Gln Ala Gln Gln Ala Gly Pro Glu Val Thr Tyr Glu Gln Ile Asn
    275                 280                 285

Asn Ala Met Val Ser Ala Lys Asp Phe Ser Gly Ala Glu Leu Tyr Thr
290                 295                 300

Leu Glu Glu Val Gln Tyr Gly Lys Phe Glu Ala Arg Met Lys Met Ala
305                 310                 315                 320

Ala Ala Ser Gly Thr Val Ser Ser Met Phe Leu Tyr Gln Asn Gly Ser
                325                 330                 335

Glu Ile Ala Asp Gly Arg Pro Trp Val Glu Val Asp Ile Glu Val Leu
            340                 345                 350

Gly Lys Asn Pro Gly Ser Phe Gln Ser Asn Ile Ile Thr Gly Lys Ala
        355                 360                 365

Gly Ala Gln Lys Thr Ser Glu Lys His His Ala Val Ser Pro Ala Ala
    370                 375                 380

Asp Gln Ala Phe His Thr Tyr Gly Leu Glu Trp Thr Pro Asn Tyr Val
385                 390                 395                 400

Arg Trp Thr Val Asp Gly Gln Glu Val Arg Lys Thr Glu Gly Gly Gln
                405                 410                 415

Val Ser Asn Leu Thr Gly Thr Gln Gly Leu Arg Phe Asn Leu Trp Ser
            420                 425                 430

Ser Glu Ser Ala Ala Trp Val Gly Gln Phe Asp Glu Ser Lys Leu Pro
        435                 440                 445

Leu Phe Gln Phe Ile Asn Trp Val Lys Val Tyr Lys Tyr Thr Pro Gly
    450                 455                 460

Gln Gly Glu Gly Gly Ser Asp Phe Thr Leu Asp Trp Thr Asp Asn Phe
465                 470                 475                 480

Asp Thr Phe Asp Gly Ser Arg Trp Gly Lys Gly Asp Phe Thr Phe Asp
                485                 490                 495

Gly Asn Arg Val Asp Leu Thr Asp Lys Asn Ile Tyr Ser Arg Asp Gly
            500                 505                 510

Met Leu Ile Leu Ala Leu Thr Arg Lys Gly Gln Glu Ser Phe Asn Gly
        515                 520                 525

Gln Val Pro Arg Asp Asp Glu Pro Ala Pro Asn Ser Ser Ser Val Asp
    530                 535                 540

Lys Leu Ala Ala Ala Leu Glu His His His His His His
545                 550                 555

<210> SEQ ID NO 6
<211> LENGTH: 1724
<212> TYPE: DNA
<213> ORGANISM: Artificial sequence
<220> FEATURE:
<223> OTHER INFORMATION: Synthetic polynucleotide

<400> SEQUENCE: 6

```
atggccatgg aggatgaaga caaagtggaa gactggcagc tcgtttggag tcaggagttc    60
gatgacggtg ttatcgatcc gaacatctgg aacttcgaga taggaaacgg tcatgcaaaa   120
ggtattccag gctggggtaa cggggaactc gagtactata cagacgaaaa cgcgttcgtt   180
gagaacggct gtcttgtgat tgaggcaaga aaagaacagg tttccgatga gtacggaacc   240
tacgactaca cctcagccag gatgaccaca gaaggaaaat cgaaataaa gtacggaaaa   300 atcgaaataa gggcaaaact tccaaaagga aaggtatct ggcccgctct ctggatgctc    360
ggaaacaaca taggagaggt cggatggccc acctgtggtg agatagacat catggaaatg   420
cttggccacg acaccagaac cgtttatgga acagcacacg gtccgggata ttctggtggt   480
gcgagtatag gtgttgccta tcatcttcca gaaggagttc ctgatttctc cgaagacttc   540
cacattttct ccatcgagtg ggacgaagac gaagtggagt ggtacgtgga cggacagctc   600
taccacgtcc tcagcaagga tgaactggcc gaactcggtc ttgagtgggt tttcgaccat   660
ccgttcttcc tcattctgaa cgttgccgtg ggaggctact ggccgggtta tcccgacgaa   720
accacccaat tcccgcagag aatgtacatc gactacatca gagtctataa agatatgaat   780
ccggaaacaa tcaccgggga agtggatgac tgcgaatatg aacaagcaca gcagcaggca   840
ggtcccgagg tgacctatga acagataaat aacgccatgg ttagcgcaaa ggatttttagc   900 ggtgccgaac tctacacgtt agaagaagtt cagtacggta agtttgaagc ccgtatgaag   960
atggcagccg catcggaaac agtcagttcc atgttcctct accagaatgg ttccgaaatc  1020
gccgatggaa ggccctgggt agaagtggat attgaagttc tcggcaagaa tccgggcagt  1080
ttccagtcca acatcattac cggtaaggcc ggcgcacaaa agactagcga aaagcaccat  1140
gctgttagcc ccgccgccga tcaggctttc cacacctacg gtctcgaatg gactccgaat  1200
tacgtccgct ggactgttga cggtcaggaa gtccgcaaga cggaaggtgg ccaggtttcc  1260
aacttgacag gtacacaggg actccgtttt aacctttggt cgtctgagag tgcggcttgg  1320
gttggccagt tcgatgaatc aaagcttccg ctttttccagt tcatcaactg ggtcaaggtt  1380
tataagtata cgccgggcca gggcgaaggc ggcagcgact ttacgcttga ctggaccgac  1440
aattttgaca cgtttgatgg ctcccgctgg ggcaagggtg acttcacatt tgacggtaac  1500
cgtgtcgacc tcaccgacaa gaacatctac tccagagatg gcatgttgat cctcgccctc  1560
acccgcaaag gtcaggaaag cttcaacggc caggttccga gagatgacga acctgccccg  1620
aattcgagct ccgtcgacaa gcttgcggcc gcactcgagc accaccacca ccaccactga  1680
gatccggctg ctaacaaagc ccgaaagaag ctgaagttct cggt               1724
```

<210> SEQ ID NO 7
<211> LENGTH: 412
<212> TYPE: PRT
<213> ORGANISM: Artificial sequence
<220> FEATURE:
<223> OTHER INFORMATION: Synthetic polypeptide

<400> SEQUENCE: 7

```
Met Val Ser Ala Lys Asp Phe Ser Gly Ala Glu Leu Tyr Thr Leu Glu
1               5                   10                  15

Glu Val Gln Tyr Gly Lys Phe Glu Ala Arg Met Lys Met Ala Ala Ala
            20                  25                  30

Ser Gly Thr Val Ser Ser Met Phe Leu Tyr Gln Asn Gly Ser Glu Ile
        35                  40                  45

Ala Asp Gly Arg Pro Trp Val Glu Val Asp Ile Glu Val Leu Gly Lys
    50                  55                  60
```

Asn Pro Gly Ser Phe Gln Ser Asn Ile Ile Thr Gly Lys Ala Gly Ala
 65                  70                  75                  80

Gln Lys Thr Ser Glu Lys His His Ala Val Ser Pro Ala Ala Asp Gln
             85                  90                  95

Ala Phe His Thr Tyr Gly Leu Glu Trp Thr Pro Asn Tyr Val Arg Trp
         100                 105                 110

Thr Val Asp Gly Gln Glu Val Arg Lys Thr Glu Gly Gly Gln Val Ser
     115                 120                 125

Asn Leu Thr Gly Thr Gln Gly Leu Arg Phe Asn Leu Trp Ser Ser Glu
 130                 135                 140

Ser Ala Ala Trp Val Gly Gln Phe Asp Glu Ser Lys Leu Pro Leu Phe
145                 150                 155                 160

Gln Phe Ile Asn Trp Val Lys Val Tyr Lys Tyr Thr Pro Gly Gln Gly
                 165                 170                 175

Glu Gly Gly Ser Asp Phe Thr Leu Asp Trp Thr Asp Asn Phe Asp Thr
             180                 185                 190

Phe Asp Gly Ser Arg Trp Gly Lys Gly Asp Phe Thr Phe Asp Gly Asn
         195                 200                 205

Arg Val Asp Leu Thr Asp Lys Asn Ile Tyr Ser Arg Asp Gly Met Leu
     210                 215                 220

Ile Leu Ala Leu Thr Arg Lys Gly Gln Glu Ser Phe Asn Gly Gln Val
225                 230                 235                 240

Pro Arg Asp Asp Glu Pro Ala Pro Asn Ser Gly Thr Phe Asp Glu Pro
                 245                 250                 255

Ile Val Asn Asp Gln Ala Asn Asn Pro Asp Glu Trp Phe Ile Trp Gln
             260                 265                 270

Ala Gly Asp Tyr Gly Ile Ser Gly Ala Arg Val Ser Asp Tyr Gly Val
         275                 280                 285

Arg Asp Gly Tyr Ala Tyr Ile Thr Ile Ala Asp Pro Gly Thr Asp Thr
     290                 295                 300

Trp His Ile Gln Phe Asn Gln Trp Ile Gly Leu Tyr Arg Gly Lys Thr
305                 310                 315                 320

Tyr Thr Ile Ser Phe Lys Ala Lys Ala Asp Thr Pro Arg Pro Ile Asn
                 325                 330                 335

Val Lys Ile Leu Gln Asn His Asp Pro Trp Thr Asn Tyr Phe Ala Gln
             340                 345                 350

Thr Val Asn Leu Thr Ala Asp Trp Gln Thr Phe Thr Phe Thr Tyr Thr
         355                 360                 365

His Pro Asp Asp Ala Asp Glu Val Val Gln Ile Ser Phe Glu Leu Gly
     370                 375                 380

Glu Gly Thr Ala Thr Thr Ile Tyr Phe Asp Asp Val Thr Val Ser Pro
385                 390                 395                 400

Gln Ala Ala Ala Leu Glu His His His His His
                 405                 410

<210> SEQ ID NO 8
<211> LENGTH: 1371
<212> TYPE: DNA
<213> ORGANISM: Artificial sequence
<220> FEATURE:
<223> OTHER INFORMATION: Synthetic polynucleotide

<400> SEQUENCE: 8 cccctttta aagggcacat tcccctctag aataatttg tttaacttta agaaggagat      60

```
atacatatga aatacctgct gccgaccgct gctgctggtc tgctgctcct cgctgcccag    120
ccggcgatgg ccatggttag cgcaaaggat tttagcggtg ccgaactcta cacgttagaa    180
gaagttcagt acggtaagtt tgaagcccgt atgaagatgg cagccgcatc gggaacagtc    240
agttccatgt tcctctacca gaatggttcc gaaatcgccg atggaaggcc ctgggtagaa    300
gtggatattg aagttctcgg caagaatccg ggcagtttcc agtccaacat cattaccggt    360
aaggccggcg cacaaaagac tagcgaaaag caccatgctg ttagccccgc cgccgatcag    420
gctttccaca cctacggtct cgaatggact ccgaattacg tccgctggac tgttgacggt    480
caggaagtcc gcaagacgga aggtggccag gtttccaact tgacaggtac acagggactc    540
cgttttaacc tttggtcgtc tgagagtgcg gcttgggttg ccagttcga tgaatcaaag    600 cttccgcttt tccagttcat caactgggtc aaggtttata agtatacgcc gggccagggc    660
gaaggcggca gcgactttac gcttgactgg accgacaatt ttgacacgtt tgatggctcc    720
cgctggggca agggtgactt cacatttgac ggtaaccgtg tcgacctcac cgacaagaac    780
atctactcca gagatggcat gttgatcctc gccctcaccc gcaaaggtca ggaaagcttc    840
aacggccagg ttccgagaga tgacgaacct gccccgaatt ccggcacttt cgacgaacct    900
attgtgaacg atcaggccaa caacccggac gaatggttca tttggcaggc gggagattac    960
gggatcagcg gtgccagggt ctccgattac ggtgtcaggg atggctacgc ttatatcacg   1020
atagccgatc ctggaactga cacgtggcat attcagttca accagtggat aggtctttac   1080
agaggaaaaa cctacaccat ttctttcaaa gcaaaagcgg atacaccaag acctataaat   1140
gtgaaaattc tgcagaatca cgatccctgg accaactatt ttgctcaaac ggtgaatctc   1200
acagcggact ggcagacgtt cacgttcacc tacacgcatc cagacgatgc ggatgaggtc   1260
gttcagatca gtttcgaact cggagaagga acggcaacta cgatttattt cgatgatgtc   1320
acggtgagcc ctcaagcggc cgcactcgag caccaccacc accaccactg a           1371
```

<210> SEQ ID NO 9
<211> LENGTH: 543
<212> TYPE: PRT
<213> ORGANISM: Artificial sequence
<220> FEATURE:
<223> OTHER INFORMATION: Synthetic polypeptide

<400> SEQUENCE: 9

```
Met Val Ser Ala Lys Asp Phe Ser Gly Ala Glu Leu Tyr Thr Leu Glu
1               5                   10                  15

Glu Val Gln Tyr Gly Lys Phe Glu Ala Arg Met Lys Met Ala Ala Ala
            20                  25                  30

Ser Gly Thr Val Ser Ser Met Phe Leu Tyr Gln Asn Gly Ser Glu Ile
        35                  40                  45

Ala Asp Gly Arg Pro Trp Val Glu Val Asp Ile Glu Val Leu Gly Lys
    50                  55                  60

Asn Pro Gly Ser Phe Gln Ser Asn Ile Ile Thr Gly Lys Ala Gly Ala
65                  70                  75                  80

Gln Lys Thr Ser Glu Lys His His Ala Val Ser Pro Ala Ala Asp Gln
            85                  90                  95

Ala Phe His Thr Tyr Gly Leu Glu Trp Thr Pro Asn Tyr Val Arg Trp
            100                 105                 110

Thr Val Asp Gly Gln Glu Val Arg Lys Thr Glu Gly Gly Gln Val Ser
            115                 120                 125

Asn Leu Thr Gly Thr Gln Gly Leu Arg Phe Asn Leu Trp Ser Ser Glu
```

```
            130                 135                 140
Ser Ala Ala Trp Val Gly Gln Phe Asp Glu Ser Lys Leu Pro Leu Phe
145                 150                 155                 160

Gln Phe Ile Asn Trp Val Lys Val Tyr Lys Tyr Thr Pro Gly Gln Gly
                165                 170                 175

Glu Gly Gly Ser Asp Phe Thr Leu Asp Trp Thr Asp Asn Phe Asp Thr
                180                 185                 190

Phe Asp Gly Ser Arg Trp Gly Lys Gly Asp Phe Thr Phe Asp Gly Asn
                195                 200                 205

Arg Val Asp Leu Thr Asp Lys Asn Ile Tyr Ser Arg Asp Gly Met Leu
            210                 215                 220

Ile Leu Ala Leu Thr Arg Lys Gly Gln Glu Ser Phe Asn Gly Gln Val
225                 230                 235                 240

Pro Arg Asp Asp Glu Pro Ala Pro Asn Ser Glu Asp Trp Gln Leu Val
                245                 250                 255

Trp Ser Gln Glu Phe Asp Asp Gly Val Ile Asp Pro Asn Ile Trp Asn
                260                 265                 270

Phe Glu Ile Gly Asn Gly His Ala Lys Gly Ile Pro Gly Trp Gly Asn
                275                 280                 285

Gly Glu Leu Glu Tyr Tyr Thr Asp Glu Asn Ala Phe Val Glu Asn Gly
            290                 295                 300

Cys Leu Val Ile Glu Ala Arg Lys Glu Gln Val Ser Asp Glu Tyr Gly
305                 310                 315                 320

Thr Tyr Asp Tyr Thr Ser Ala Arg Met Thr Thr Glu Gly Lys Phe Glu
                325                 330                 335

Ile Lys Tyr Gly Lys Ile Glu Ile Arg Ala Lys Leu Pro Lys Gly Lys
                340                 345                 350

Gly Ile Trp Pro Ala Leu Trp Met Leu Gly Asn Asn Ile Gly Glu Val
                355                 360                 365

Gly Trp Pro Thr Cys Gly Glu Ile Asp Ile Met Glu Met Leu Gly His
            370                 375                 380

Asp Thr Arg Thr Val Tyr Gly Thr Ala His Gly Pro Gly Tyr Ser Gly
385                 390                 395                 400

Gly Ala Ser Ile Gly Val Ala Tyr His Leu Pro Glu Gly Val Pro Asp
                405                 410                 415

Phe Ser Glu Asp Phe His Ile Phe Ser Ile Glu Trp Asp Glu Asp Glu
                420                 425                 430

Val Glu Trp Tyr Val Asp Gly Gln Leu Tyr His Val Leu Ser Lys Asp
            435                 440                 445

Glu Leu Ala Glu Leu Gly Leu Glu Trp Val Phe Asp His Pro Phe Phe
450                 455                 460

Leu Ile Leu Asn Val Ala Val Gly Gly Tyr Trp Pro Gly Tyr Pro Asp
465                 470                 475                 480

Glu Thr Thr Gln Phe Pro Gln Arg Met Tyr Ile Asp Tyr Ile Arg Val
                485                 490                 495

Tyr Lys Asp Met Asn Pro Glu Thr Ile Thr Gly Glu Val Asp Asp Cys
                500                 505                 510

Glu Tyr Glu Gln Ala Gln Gln Ala Gly Pro Glu Val Thr Tyr Glu
                515                 520                 525

Gln Ile Asn Asn Ala Ala Ala Leu Glu His His His His His His
            530                 535                 540

<210> SEQ ID NO 10
```

<211> LENGTH: 1804
<212> TYPE: DNA
<213> ORGANISM: Artificial sequence
<220> FEATURE:
<223> OTHER INFORMATION: Synthetic polynucleotide

<400> SEQUENCE: 10

```
gaatgggata acggaaattc cctctagaat aattttgttt aactttaaga aggagatata      60
catatgaaat acctgctggc gaccgctgct gctggtctgc tgctcctcgc tgcccagccg     120
gcgatggcca tggttagcgc aaaggatttt agcggtgccg aactctacac gttagaagaa     180
gttcagtacg gtaagtttga agcccgtatg aagatggcag ccgcatcggg aacagtcagt     240
tccatgttcc tctaccagaa tggttccgaa atcgccgatg aaggccctg ggtagaagtg      300
gatattgaag ttctcggcaa gaatccgggc agtttccagt ccaacatcat taccggtaag     360
gccggcgcac aaaagactag cgaaaagcac catgctgtta gccccgccgc cgatcaggct     420
ttccacacct acggtctcga atggactccg aattacgtcc gctggactgt tgacggtcag     480
gaagtccgca gacggaagg tggccaggtt tccaacttga caggtacaca gggactccgt      540
tttaaccttt ggtcgtctga gagtgcggct tgggttggcc agttcgatga atcaaagctt     600
ccgcttttcc agttcatcaa ctgggtcaag gtttataagt atacgccggg ccagggcgaa     660
ggcggcagcg actttacgct tgactggacc gacaattttg acacgtttga tggctcccgc     720
tggggcaagg gtgacttcac atttgacggt aaccgtgtcg acctcaccga caagaacatc     780
tactccagag atggcatgtt gatcctcgcc ctcacccgca aggtcaagaa agcttcaac      840
ggccaggttc cgagagatga cgaacctgct ccgaattcgg aagactggca gctcgtttgg     900
agtcaggagt tcgatgacgg tgttatcgat ccgaacatct ggaacttcga gataggaaac     960
ggtcatgcaa aaggtattcc aggctggggt aacggggaac tcgagtacta tacagacgaa    1020
aacgcgttcg ttgagaacgg ctgtcttgtg attgaggcaa gaaaagaaca ggtttccgat    1080
gagtacggaa cctacgacta cacctcagcc aggatgacca cagaaggaaa attcgaaata    1140
aagtacggaa aaatcgaaat aagggcaaaa cttccaaaag gaaaaggtat ctggcccgct    1200
ctctggatgc tcggaaacaa cataggagag gtcggatggc ccacctgtgg tgagatagac    1260
atcatggaaa tgcttggcca cgacaccaga accgtttatg gaacagcaca cggtccggga    1320
tattctggtg gtgcgagtat aggtgttgcc tatcatcttc cagaaggagt tcctgatttc    1380
tccgaagact ccacattttt ctccatcgag tgggacgaag acgaagtgga gtggtacgtg    1440
gacggacagc tctaccacgt cctcagcaag gatgaactgg ccgaactcgg tcttgagtgg    1500
gttttcgacc atccgttctt cctcattctg aacgttgccg tgggaggcta ctggccgggt    1560
tatcccgacg aaaccaccca attcccgcag agaatgtaca tcgactacat cagagtctat    1620
aaagatatga atccggaaac aatcaccggg gaagtggatg actgcgaata tgaacaagca    1680
cagcagcagg caggtcccga ggtgacctat gaacagataa ataacgcggc cgcactcgag    1740
caccaccacc accaccactg agatccggct gctaacaaag cccgaaagaa gctaagtgcg    1800
ggaa                                                                 1804
```

<210> SEQ ID NO 11
<211> LENGTH: 598
<212> TYPE: PRT
<213> ORGANISM: Artificial sequence
<220> FEATURE:
<223> OTHER INFORMATION: Synthetic polypeptide

<400> SEQUENCE: 11

-continued

```
Met Ala Gln Asn Ile Leu Gly Asn Ala Ser Phe Asp Glu Pro Ile Leu
1               5                   10                  15

Ile Ala Gly Val Asp Ile Asp Pro Pro Ala Glu Asp Gly Ser Ile Asp
            20                  25                  30

Thr Gly Gly Asn Trp Val Phe Phe Thr Asn Ser Asn Gly Glu Gly Thr
        35                  40                  45

Ala Arg Val Glu Asn Gly Val Leu Val Val Glu Ile Thr Asn Gly Gly
    50                  55                  60

Asp His Thr Trp Ser Val Gln Ile Ile Gln Ala Pro Ile Arg Val Glu
65                  70                  75                  80

Lys Leu His Lys Tyr Arg Val Ser Phe Arg Ala Lys Ala Ser Ser Gln
                85                  90                  95

Lys Asn Ile Gly Val Lys Ile Gly Gly Thr Ala Gly Arg Gly Trp Thr
            100                 105                 110

Ala Tyr Asn Pro Gly Thr Asp Glu Ser Gly Gly Met Val Phe Glu Leu
        115                 120                 125

Gly Thr Asp Trp Gln Lys Tyr Glu Phe Glu Phe Val Met Arg Gln Glu
    130                 135                 140

Thr Asp Glu Asn Ala Arg Phe Glu Phe Gln Leu Gly Arg Tyr Thr Gly
145                 150                 155                 160

Thr Val Trp Ile Asp Asp Val Val Met Glu Asp Ile Gly Val Leu Glu
                165                 170                 175

Val Ser Gly Glu Glu Asn Glu Ile Tyr Thr Met Val Ser Ala Lys Asp
            180                 185                 190

Phe Ser Gly Ala Glu Leu Tyr Thr Leu Glu Glu Val Gln Tyr Gly Lys
        195                 200                 205

Phe Glu Ala Arg Met Lys Met Ala Ala Ala Ser Gly Thr Val Ser Ser
    210                 215                 220

Met Phe Leu Tyr Gln Asn Gly Ser Glu Ile Ala Asp Gly Arg Pro Trp
225                 230                 235                 240

Val Glu Val Asp Ile Glu Val Leu Gly Lys Asn Pro Gly Ser Phe Gln
                245                 250                 255

Ser Asn Ile Ile Thr Gly Lys Ala Gly Ala Gln Lys Thr Ser Glu Lys
            260                 265                 270

His His Ala Val Ser Pro Ala Ala Asp Gln Ala Phe His Thr Tyr Gly
        275                 280                 285

Leu Glu Trp Thr Pro Asn Tyr Val Arg Trp Thr Val Asp Gly Gln Glu
    290                 295                 300

Val Arg Lys Thr Glu Gly Gly Gln Val Ser Asn Leu Thr Gly Thr Gln
305                 310                 315                 320

Gly Leu Arg Phe Asn Leu Trp Ser Ser Glu Ser Ala Ala Trp Val Gly
                325                 330                 335

Gln Phe Asp Glu Ser Lys Leu Pro Leu Phe Gln Phe Ile Asn Trp Val
            340                 345                 350

Lys Val Tyr Lys Tyr Thr Pro Gly Gln Gly Glu Gly Ser Asp Phe
        355                 360                 365

Thr Leu Asp Trp Thr Asp Asn Phe Asp Thr Phe Asp Gly Ser Arg Trp
    370                 375                 380

Gly Lys Gly Asp Phe Thr Phe Asp Gly Asn Arg Val Asp Leu Thr Asp
385                 390                 395                 400

Lys Asn Ile Tyr Ser Arg Asp Gly Met Leu Ile Leu Ala Leu Thr Arg
                405                 410                 415
```

```
Lys Gly Gln Glu Ser Phe Asn Gly Gln Val Pro Arg Asp Asp Glu Pro
                420                 425                 430

Ala Pro Asn Ser Gly Thr Phe Asp Glu Pro Ile Val Asn Asp Gln Ala
            435                 440                 445

Asn Asn Pro Asp Glu Trp Phe Ile Trp Gln Ala Gly Asp Tyr Gly Ile
        450                 455                 460

Ser Gly Ala Arg Val Ser Asp Tyr Gly Val Arg Asp Gly Tyr Ala Tyr
465                 470                 475                 480

Ile Thr Ile Ala Asp Pro Gly Thr Asp Thr Trp His Ile Gln Phe Asn
                485                 490                 495

Gln Trp Ile Gly Leu Tyr Arg Gly Lys Thr Tyr Thr Ile Ser Phe Lys
            500                 505                 510

Ala Lys Ala Asp Thr Pro Arg Pro Ile Asn Val Lys Ile Leu Gln Asn
        515                 520                 525

His Asp Pro Trp Thr Asn Tyr Phe Ala Gln Thr Val Asn Leu Thr Ala
530                 535                 540

Asp Trp Gln Thr Phe Thr Phe Tyr Thr His Pro Asp Asp Ala Asp
545                 550                 555                 560

Glu Val Val Gln Ile Ser Phe Glu Leu Gly Glu Gly Thr Ala Thr Thr
                565                 570                 575

Ile Tyr Phe Asp Asp Val Thr Val Ser Pro Gln Ala Ala Ala Leu Glu
            580                 585                 590

His His His His His His
        595

<210> SEQ ID NO 12
<211> LENGTH: 1930
<212> TYPE: DNA
<213> ORGANISM: Artificial sequence
<220> FEATURE:
<223> OTHER INFORMATION: Synthetic polynucleotide

<400> SEQUENCE: 12
cgctctatac ccgaaaaaat ttcccttcta gactaatttt gtttaacttt aagaaggaga      60
tatacatatg aaatacctgc tgccgaccgc tgctgctggt ctgctgctcc tcgctgccca     120
gccggcgatg gccatggctc aaaacatcct tggcaacgct tctttcgatg aaccaattct     180
catcgcaggt gtggatatag acccacccgc agaggatggc tctatagaca caggaggaaa     240
ctgggtattc ttcaccaatt caaacggtga gggaacggct cgagtcgaaa acggcgttct     300
cgtggttgag ataacaaacg gaggagatca cacctggtcg gttcgagatca tacaggctcc     360 catacgtgtt gagaaactcc acaagtacag agtttctttc cgagccaagg cttcctctca     420
aaagaacatc gggtgaaga taggaggaac ggccggaaga ggatggaccg cgtacaaccc     480
cggtaccgac gaatccggcg gcatggtctt cgagctcgga acagattggc agaagtacga     540
gttcgaattc gtcatgagac aggagaccga tgaaaatgct cgtttcgagt ttcagcttgg     600
aaggtatacc ggcacggtct ggatagacga cgtagtgatg gaggacatcg gtgttctcga     660
ggtaagcggt gaggaaaacg aaatctacac catggttagc gcaaaggatt ttagcggtgc     720
cgaactctac acgttagaag aagttcagta cggtaagttt gaagcccgta tgaagatggc     780
agccgcatcg ggaacagtca gttccatgtt cctctaccag aatggttccg aaatcgccga     840
tggaaggccc tgggtagaag tggatattga agttctcggc aagaatccgg gcagtttcca     900
gtccaacatc attaccggta aggccggcgc acaaaagact agcgaaaagc accatgctgt     960
tagccccgcc gccgatcagg cttttccacac ctacggtctc gaatggactc cgaattacgt    1020
```

```
ccgctggact gttgacggtc aggaagtccg caagacggaa ggtggccagg tttccaactt    1080
gacaggtaca cagggactcc gttttaacct ttggtcgtct gagagtgcgg cttgggttgg    1140
ccagttcgat gaatcaaagc ttccgctttt ccagttcatc aactgggtca aggtttataa    1200
gtatacgccg ggccagggcg aaggcggcag cgactttacg cttgactgga ccgacaattt    1260
tgacacgttt gatggctccc gctggggcaa gggtgacttc acatttgacg gtaaccgtgt    1320
cgacctcacc gacaagaaca tctactccag agatggcatg ttgatcctcg ccctcacccg    1380
caaaggtcag gaaagcttca acggccaggt tccgagagat gacgaacctg ccccgaattc    1440
cggcactttc gacgaaccta tgtgaacga tcaggccaac aacccggacg aatggttcat    1500
ttggcaggcg ggagattacg ggatcagcgg tgccagggtc tccgattacg gtgtcaggga    1560
tggctacgct tatatcacga tagccgatcc tggaactgac acgtggcata ttcagttcaa    1620
ccagtggata ggtctttaca gaggaaaaac ctacaccatt tctttcaaag caaaagcgga    1680
tacaccaaga cctataaatg tgaaaattct gcagaatcac gatccctgga ccaactattt    1740
tgctcaaacg gtgaatctca gcggactg gcagacgttc acgttcacct acacgcatcc    1800
agacgatgcg gatgaggtcg ttcagatcag tttcgaactc ggagaaggaa cggcaactac    1860
gatttatttc gatgatgtca cggtgagccc tcaagcggcc gcactcgagc accaccacca    1920
ccaccactga                                                           1930
```

<210> SEQ ID NO 13
<211> LENGTH: 453
<212> TYPE: PRT
<213> ORGANISM: Artificial sequence
<220> FEATURE:
<223> OTHER INFORMATION: Synthetic polypeptide

<400> SEQUENCE: 13

```
Met Ala Gln Asn Ile Leu Gly Asn Ala Ser Phe Asp Glu Pro Ile Leu
1               5                   10                  15

Ile Ala Gly Val Asp Ile Asp Pro Pro Ala Glu Asp Gly Ser Ile Asp
            20                  25                  30

Thr Gly Gly Asn Trp Val Phe Phe Thr Asn Ser Asn Gly Glu Gly Thr
        35                  40                  45

Ala Arg Val Glu Asn Gly Val Leu Val Val Glu Ile Thr Asn Gly Gly
    50                  55                  60

Asp His Thr Trp Ser Val Gln Ile Ile Gln Ala Pro Ile Arg Val Glu
65                  70                  75                  80

Lys Leu His Lys Tyr Arg Val Ser Phe Arg Ala Lys Ala Ser Ser Gln
                85                  90                  95

Lys Asn Ile Gly Val Lys Ile Gly Gly Thr Ala Gly Arg Gly Trp Thr
            100                 105                 110

Ala Tyr Asn Pro Gly Thr Asp Glu Ser Gly Gly Met Val Phe Glu Leu
        115                 120                 125

Gly Thr Asp Trp Gln Lys Tyr Glu Phe Glu Phe Val Met Arg Gln Glu
    130                 135                 140

Thr Asp Glu Asn Ala Arg Phe Glu Phe Gln Leu Gly Arg Tyr Thr Gly
145                 150                 155                 160

Thr Val Trp Ile Asp Asp Val Met Glu Asp Ile Gly Val Leu Glu
                165                 170                 175

Val Ser Gly Glu Glu Asn Glu Ile Tyr Thr Met Val Ser Ala Lys Asp
            180                 185                 190
```

Phe Ser Gly Ala Glu Leu Tyr Thr Leu Glu Glu Val Gln Tyr Gly Lys
            195                 200                 205

Phe Glu Ala Arg Met Lys Met Ala Ala Ser Gly Thr Val Ser Ser
            210                 215                 220

Met Phe Leu Tyr Gln Asn Gly Ser Glu Ile Ala Asp Gly Arg Pro Trp
225                 230                 235                 240

Val Glu Val Asp Ile Glu Val Leu Gly Lys Asn Pro Gly Ser Phe Gln
                245                 250                 255

Ser Asn Ile Ile Thr Gly Lys Ala Gly Ala Gln Lys Thr Ser Glu Lys
            260                 265                 270

His His Ala Val Ser Pro Ala Ala Asp Gln Ala Phe His Thr Tyr Gly
            275                 280                 285

Leu Glu Trp Thr Pro Asn Tyr Val Arg Trp Thr Val Asp Gly Gln Glu
            290                 295                 300

Val Arg Lys Thr Glu Gly Gly Gln Val Ser Asn Leu Thr Gly Thr Gln
305                 310                 315                 320

Gly Leu Arg Phe Asn Leu Trp Ser Ser Glu Ser Ala Ala Trp Val Gly
                325                 330                 335

Gln Phe Asp Glu Ser Lys Leu Pro Leu Phe Gln Phe Ile Asn Trp Val
            340                 345                 350

Lys Val Tyr Lys Tyr Thr Pro Gly Gln Gly Glu Gly Ser Asp Phe
            355                 360                 365

Thr Leu Asp Trp Thr Asp Asn Phe Asp Thr Phe Asp Gly Ser Arg Trp
            370                 375                 380

Gly Lys Gly Asp Phe Thr Phe Asp Gly Asn Arg Val Asp Leu Thr Asp
385                 390                 395                 400

Lys Asn Ile Tyr Ser Arg Asp Gly Met Leu Ile Leu Ala Leu Thr Arg
                405                 410                 415

Lys Gly Gln Glu Ser Phe Asn Gly Gln Val Pro Arg Asp Asp Glu Pro
            420                 425                 430

Ala Pro Asn Ser Ser Ser Val Asp Lys Leu Ala Ala Ala Leu Glu His
            435                 440                 445

His His His His His
    450

<210> SEQ ID NO 14
<211> LENGTH: 1493
<212> TYPE: DNA
<213> ORGANISM: Artificial sequence
<220> FEATURE:
<223> OTHER INFORMATION: Synthetic polynucleotide

<400> SEQUENCE: 14
tttaagaagg agatatacat atgaaatacc tgctgccgac cgctgctgct ggtctgctgc    60
tcctcgctgc ccagccggcg atggccatgg ctcaaaacat ccttggcaac gcttctttcg   120
atgaaccaat tctcatcgca ggtgtggata tagacccacc cgcagaggat ggctctatag   180
acacaggagg aaactgggta ttcttcacca attcaaacgg tgagggaacg gctcgagtcg   240
aaaacggcgt tctcgtggtt gagataacaa acggaggaga tcacacctgg tcggttcaga   300
tcatacaggc tcccatacgt gttgagaaac tccacagta cagagtttct ttccgagcca   360
aggcttcctc tcaaaagaac atcggggtga agataggagg aacggccgga agaggatgga   420
ccgcgtacaa ccccggtacc gacgaatccg gcggcatggt cttcgagctc ggaacagatt   480
ggcagaagta cgagttcgaa ttcgtcatga gacaggagac cgatgaaaat gctcgtttcg   540

```
agtttcagct tggaaggtat accggcacgg tctggataga cgacgtagtg atggaggaca    600
tcggtgttct cgaggtaagc ggtgaggaaa acgaaatcta caccatggtt agcgcaaagg    660
attttagcgg tgccgaactc tacacgttag aagaagttca gtacggtaag tttgaagccc    720
gtatgaagat ggcagccgca tcgggaacag tcagttccat gttcctctac cagaatggtt    780
ccgaaatcgc cgatggaagg ccctgggtag aagtggatat tgaagttctc ggcaagaatc    840
cgggcagttt ccagtccaac atcattaccg gtaaggccgg cgcacaaaag actagcgaaa    900
agcaccatgc tgttagcccc gccgccgatc aggctttcca cacctacggt ctcgaatgga    960
ctccgaatta cgtccgctgg actgttgacg gtcaggaagt ccgcaagacg gaaggtggcc    1020
aggtttccaa cttgacaggt acacagggac tccgttttaa cctttggtcg tctgagagtg    1080
cggcttgggt tggccagttc gatgaatcaa agcttccgct tttccagttc atcaactggg    1140
tcaaggttta taagtatacg ccgggccagg gcgaaggcgg cagcgacttt acgcttgact    1200
ggaccgacaa ttttgacacg tttgatggct cccgctgggg caagggtgac ttcacatttg    1260
acggtaaccg tgtcgacctc accgacaaga acatctactc cagagatggc atgttgatcc    1320
tcgccctcac ccgcaaaggt caggaaagct caacggcca ggttccgaga gatgacgaac     1380
ctgccccgaa ttcgagctcc gtcgacagc ttgcggccgc actcgagcac caccaccac     1440 accactgaga tccggctgct aacaaagccc gaaagaagct agggttttc gtc            1493
```

<210> SEQ ID NO 15
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 15

```
cctgttttca ccatggctca aaacatcctt ggc                                 33
```

<210> SEQ ID NO 16
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 16

```
gcaccgggga tgcggccgct tgagggctc                                      29
```

<210> SEQ ID NO 17
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 17

```
ggatgaagag aatcggaaga ctggc                                          25
```

<210> SEQ ID NO 18
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 18

```
cgaaatctac accatggagg atgaagac                                       28
```

```
<210> SEQ ID NO 19
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 19
gtcttcatcc tccatggtgt agatttcg                                    28

<210> SEQ ID NO 20
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 20
cctatgaaca gatgaattcc ggcactttcg                                  30

<210> SEQ ID NO 21
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 21
cgaaagtgcc aagctttatc tgttcatagg                                  30

<210> SEQ ID NO 22
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 22
cgaccatggc gttatttatc tgttcatagg                                  30

<210> SEQ ID NO 23
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 23
gcggccgcgt tattatctgt tcatagg                                     27

<210> SEQ ID NO 24
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 24
aaatacctgc tgccgaccg                                              19

<210> SEQ ID NO 25
<211> LENGTH: 21
<212> TYPE: DNA
<213> ORGANISM: Artificial sequence
<220> FEATURE:
```

```
<223> OTHER INFORMATION: Synthetic oligonucleotide

<400> SEQUENCE: 25
gctagttatt gctcagcggt g                                          21
```